(12) United States Patent
Sharma et al.

(10) Patent No.: US 9,855,183 B2
(45) Date of Patent: Jan. 2, 2018

(54) EYE MASSAGE DEVICE

(71) Applicant: EYE COMFORT LIMITED, Belfast, Antrim (GB)

(72) Inventors: Anant Sharma, Bedford (GB); Benjamin Anand Ruben Sharma, Bedford (GB); Jonathan Moore, Ballyclare (GB); Laurent Le Mentec, Bristol (GB); Ginny Conde, Milton Keynes (GB)

(73) Assignee: EYE COMFORT LIMITED, Belfast, Antrim (GB)

( * ) Notice: Subject to any disclaimer, the term of this patent is extended or adjusted under 35 U.S.C. 154(b) by 393 days.

(21) Appl. No.: 14/376,186

(22) PCT Filed: Feb. 1, 2013

(86) PCT No.: PCT/GB2013/050231
§ 371 (c)(1),
(2) Date: Aug. 1, 2014

(87) PCT Pub. No.: WO2013/114127
PCT Pub. Date: Aug. 8, 2013

(65) Prior Publication Data
US 2014/0378878 A1    Dec. 25, 2014

(30) Foreign Application Priority Data

Feb. 3, 2012   (GB) .................................... 1201934.5
Dec. 14, 2012  (GB) .................................... 1222560.3

(51) Int. Cl.
*A61H 5/00* (2006.01)
*A61H 7/00* (2006.01)
(Continued)

(52) U.S. Cl.
CPC ............... *A61H 5/00* (2013.01); *A61H 7/001* (2013.01); *A61F 9/00772* (2013.01);
(Continued)

(58) Field of Classification Search
CPC .. A61H 5/00; A61H 7/001; A61H 2201/0157; A61H 2201/0228;
(Continued)

(56) References Cited

U.S. PATENT DOCUMENTS 793,004 A     6/1905  May
4,303,063 A  12/1981  Stahl
(Continued)

FOREIGN PATENT DOCUMENTS

FR    813 603      6/1937
JP    2002 253631  9/2002
WO    2009/066077  5/2009

OTHER PUBLICATIONS

International Search Report and Written Opinion for International Patent Application No. PCT/GB2013/050231 dated May 2, 2013 (14 pages).
(Continued)

*Primary Examiner* — Quang D Thanh
(74) *Attorney, Agent, or Firm* — Andrus Intellectual Property Law, LLP

(57) ABSTRACT

A manual device for massaging one or both of the upper and lower lids of the eye, the device including: a body, composed of flexible resilient biocompatible material, wherein the body provides jaws or lips, wherein the lips are biased into a spaced relationship by the material of the body, and wherein each lip is adapted to engage either the upper or lower eyelid, such that movement of the lips causes movement of at least one eyelid with respect to the other. The devices can conveniently be used to manipulate the mei-
(Continued)

bomian glands of the eye in an optimum orientation, for example for alleviating or treating dry eye.

35 Claims, 13 Drawing Sheets

(51) Int. Cl.
 *A61H 23/02* (2006.01)
 *A61F 9/007* (2006.01)
(52) U.S. Cl.
 CPC .. *A61H 23/0245* (2013.01); *A61H 2201/0157* (2013.01); *A61H 2201/0207* (2013.01); *A61H 2201/0228* (2013.01); *A61H 2201/1253* (2013.01); *A61H 2201/1692* (2013.01)
(58) Field of Classification Search
 CPC .... A61H 2201/1253; A61H 2201/1692; A61H 2201/0207; A61H 23/0245; A61H 2205/024; A61F 9/00772
 See application file for complete search history.

(56) References Cited

U.S. PATENT DOCUMENTS

| | | | |
|---|---|---|---|
| 4,554,911 A | 11/1985 | Nielsen | |
| 7,069,084 B2 | 6/2006 | Yee | |
| 7,981,147 B2 | 7/2011 | Korb et al. | |
| D645,565 S | 9/2011 | Smith | |
| 8,025,689 B2 | 9/2011 | Korb et al. | |
| 8,128,673 B2 | 3/2012 | Korb et al. | |
| 2003/0056281 A1 | 3/2003 | Hasegawa | |
| 2005/0220742 A1 | 10/2005 | Breen | |
| 2006/0206041 A1 | 10/2006 | Liu | |
| 2007/0016254 A1 | 1/2007 | Grenon et al. | |
| 2007/0027431 A1* | 2/2007 | Korb | A61F 7/02 604/289 |
| 2008/0046048 A1* | 2/2008 | Grenon | A61F 7/02 607/108 |
| 2008/0114426 A1* | 5/2008 | Korb | A61F 9/00772 607/96 |
| 2010/0256552 A1 | 10/2010 | Korb et al. | |
| 2010/0285155 A1 | 11/2010 | Gilbard et al. | |
| 2012/0165708 A1 | 6/2012 | Parsloe | |

OTHER PUBLICATIONS

Conde, G.T., thesis: "Development of a Medical Device for the Treatment of Meibomian Gland Dysfunction", School of Applied Sciences, Cranfield University, Nov. 2012.

Knop, E. et al, Investigative Ophthalmology & Visual Science, Special Issue, 52 (4), 1938-1978 (2011).

Le Mentec, L., thesis: "New Product Development of a Medical Device for Dry Eyes Relief", School of Applied Science, Sep. 2012.

\* cited by examiner

Figure 1:
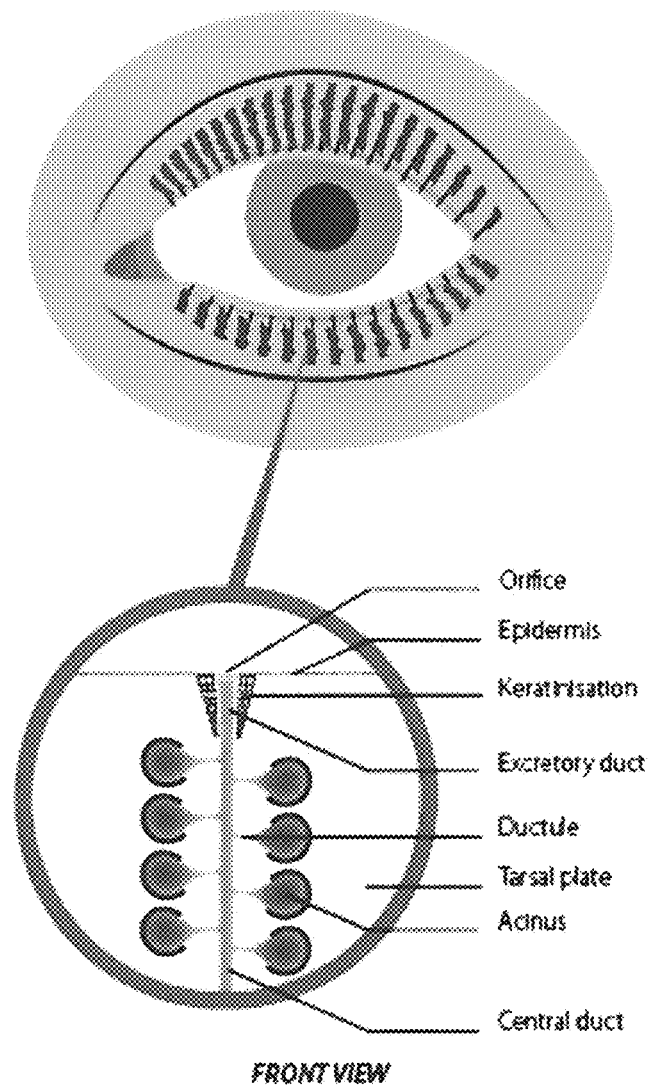
Figure 1:
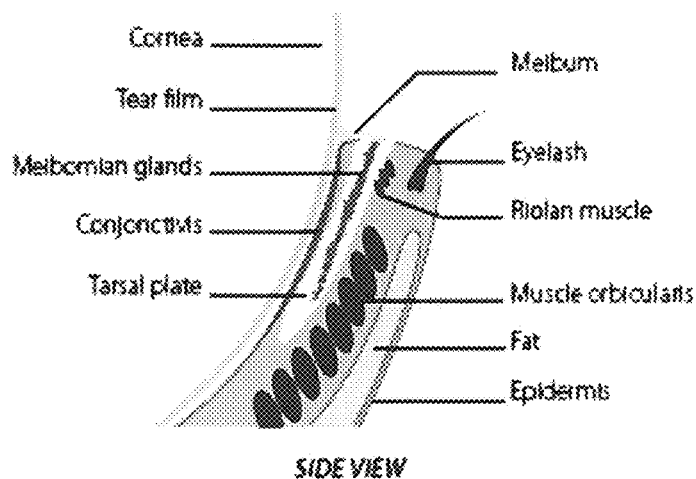

Fig. 1. Position and anatomy of the Meibomian glands

House of Quality

SOME SHAPE VARIATIONS OF THE EYE MASSAGER

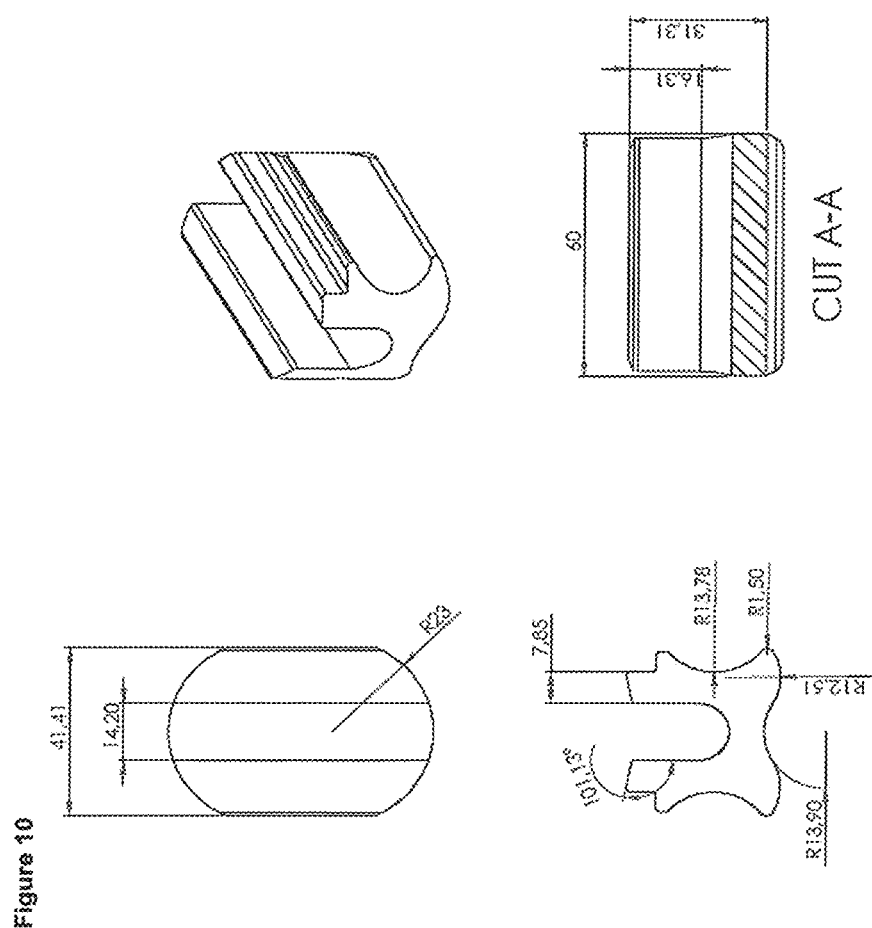

EYE MASSAGE DEVICE

CROSS-REFERENCE TO RELATED APPLICATIONS

This patent application is a national stage filing under 35 U.S.C. 371 of International Application No.PCT/GB2013/050231, filed Feb. 1, 2013, which claims the benefit of priority of Great Britain Application No. 1222560.3, filed Dec. 14, 2012, and of Great Britain Application No. 1201934.5, filed Feb. 3, 2012, all of which are incorporated herein by reference in their entireties.

TECHNICAL FIELD

The present invention relates generally to a device for eyelid massage, and processes for producing the same, and methods of use thereof.

BACKGROUND ART

A study estimated that 4.3 million Americans between 65 and 83 experience dry eyes symptoms (Schein et al., 1997). With population aging, more and more people are likely to be affected. Most of the time, this condition is caused by a dysfunction of Meibomian Glands. Dry eyes are very painful and can spoil the quality of life of patients. Itching, burning eyes, blurred vision and increased risk of infection are part of their everyday life. Air conditioning, computer work, wind and dust are contributory factors that trigger the painful symptoms. The condition may be critical in some office or outside workers.

The secretion produced by Meibomian Glands is an oily liquid made of wax and sterols esters, fatty acids and fatty alcohols (Knop et al., 2011; Butovich, 2011). The secretion forms a 0.1 μm lipid film on the cornea, over the tears (Korb et al., 1994; Norn, 1979). Its functions are to provide a surfactant on the eye surface, to reduce tear evaporation, and to prevent contamination of the eye by other substances or bacteria (Mudgil and Millar, 2011; Bron et al., 2004; Driver and Lemp, 1996). Due to its variety of chemical components, the melting point of Meibomian oil is a range. Bron et al. (2004) summarized five previous studies and proposed the melting temperature ranging from 19.5 to 32.9° C.±0.9° C. for normal glands. It is also stated that the range can extend up to 40° C. in the "presence of keratinized epithelial debris within the expressed material" (Bron et al., 2004; Terada et al., 2004; Gutgesell et al., 1982; Jester et al., 1981). The viscosity of the secretion is within the 9.7-19.5 Pa·s range at 30° C. (which is comparable to honey). The secretion exhibits shear thinning non-Newtonian properties, its viscosity decreases (down to 0.1 mPa·s) when a shearing force is applied (similar to the behaviour of ketchup when a bottle is squeezed). This behaviour makes it easier to release the meibum during blinking (which has the effect of "milking" the glands. In case of Meibomian Gland Dysfunction (MGD) or chalazion, viscosity can increase significantly (69.9 Pa·s, measured at 70° C.) (Knop et al., 2011) preventing the release of secretion.

The two main causes of MGD are the hyperkeratinisation of the ducts and the degeneration of the acini cells (Knop et al., 2011). Keratin fibres are produced to rigidify the excretory duct at the border of the eyelid. In case of hyperkeratinisation, the external duct diameter is reduced or completely blocked. The pressure increases in the gland and atrophies the acini cells. The second cause is the degeneration of the acini cells. Meibum synthesis is degraded and the quantity and the quality of secretion decreases. The liquid is more viscous, often compared to toothpaste (Tomlinson et al., 2011), and loses some of its surfactant properties. These two phenomena lead to the obstruction of the glands. The process can be summarized as several vicious circles (Knop et al., 2011).

The consequence of MGD is a shortage of oil in the eye surface. This results in tears evaporating 30% quicker than an unaffected eye (Bron et al., 2004), and an uneven optical surface of the eye. For the patient this translates into: bad vision, difficult blinking, dry eye, increased risk of infection, irritation, itching, and the inability to wear contact lenses (Driver and Lemp., 1996)

It is unclear what proportion of the entire population is affected by gland dysfunction. Whilst many studies have been carried out, they target different groups of people or use different criteria, which prevents accurate comparisons and precludes definite conclusions being drawn (Schaumberg et al., 2011). As an example, the prevalence of MGD ranges from 20% in a British study (Ong and Larke, 1990) to 60% in a Japanese one (Shimazaki et al., 1995). Notwithstanding this, numerous studies establish aging as the main factor for MGD. It has been recognised for a long time that MGD probability increases with age and MGD is more common after 50 years of age (Hykin and Bron, 1992; Hom et al., 1990; Den et al., 2006). Other factors, including medicines and other external potential causes were studied, but correlations are hard to establish (Schaumberg et al., 2011).

For the most part, existing dry eye treatments are home-based. The market offers a wide array of heat masks, pads, bags and compresses. These solutions are focussed on heating and/or moisturising the eyelids. The devices usually have to be placed in a microwave oven to accumulate heat. Patients can also access a range of goggles that prevent tear evaporation during the night. Other treatments include artificial tears and special "shampoo" or gels to scrub the eyelids. Cotton buds can be used to clean the lid margins. A few antibiotics exist but they have undesirable side effects.

A non-limiting list of existing treatments include:

The Lipi flow thermal pulsation treatment produced by TearScience® is a machine composed of an ocular component and a hand held control system. The ocular component is consisting of a lid warmer providing heat (41° C. to 43° C.) an eye cup that compresses the eye lid to express the meibomian gland.

There is also the I Heat portable warm compress mask. This is an eye mask that comes with a disposable warming unit that is activated by the user.

Another mask is the Fire & Ice mask by Rhein Medical the mask is placed in the microwave for under 15 secs and then the user can use it for the warm compress it can also be used for cold compress.

Another treatment is by the use of the Blephasteam®, a device based from the studies of DR J. R. Fuller. It is a goggle that gives off moisture and heat as a result of the steam it produces.

A further treatment is simply a warm compress self-treatment, carried out by patients according to the advice of their ophthalmologists. This typically involves warm compress achieved by the traditional method of using hot cloth followed by a massage using the finger to be done on a regular basis.

The Infrared warm compression device (IWCD, Eye Hot, Cept Co, Tokyo, Japan) is an electrically powered device composed of two eye patches each incorporating 19 LEDs emitting 850 to 1050 nm.

A non-limiting list of examples of patent or design applications relating to heat or massage treatments is given below: GILBARD et al, 'Cleanser composition and methods for using the same', US 2010/0285155; LIU, H. C., 'Eyes massage device', US 2006/0206041; NIELSEN, M. J., 'Massaging tool and method for lower-eyelids and zygomatic skin', U.S. Pat. No. 4,554,911; PARSLOE, C., 'Massage apparatus and method of use', US 2012/0165708; YEE, R. W., 'Method and apparatus for preventing and treating eyelid problems', U.S. Pat. No. 7,069,084; BREEN, E. V., 'Compositions and methods for maintaining eyelid hygiene', US 2005/0220742; KNOP et al, 'The International workshop on meibomian gland dysfunction: report of the subcommittee on anatomy, physiology, and pathophysiology of the meibomian gland', IOVS 2011; SMITH, et al, 'Device for stimulating the meibomian glands of the eyelid', U.S. D645,565; KORB, et al, 'Method and apparatus for treating meibomian gland dysfunction', U.S. Pat. No. 8,025,689; STAHL, N. O., 'Ocular massage device', U.S. Pat. No. 4,303,063; KORB, et al., 'Outer eyelid heat and pressure treatment for treating meibomian gland dysfunction', U.S. Pat. No. 7,981,147; KORB. et al., 'System for inner eyelid heat and pressure treatment for treating meibomian gland dysfunction', U.S. Pat. No. 8,128,673; MAY, F. H., 'Eye-massage machine', forming part of 793,004 (1905).

Thus it can be seen that the provision of new and effective treatments for dry eye would provide a contribution to the art. Furthermore eye massage has a number of other potential cosmetic and therapeutic benefits. Therefore the provision of an eye massage device which was simple and convenient to use would also be highly beneficial.

DISCLOSURE OF THE INVENTION

As described hereinafter, primary patient research has demonstrated that sufferers of dry eye (MGD) who have been advised to perform eye massage have not been taught how to carry out eye massage properly. Furthermore it is known that if not carried out properly, the massage can lead to adverse responses and complications (McMonnies et al., 2012).

Thus, despite massaging being an important part in the treatment of MGD, a relative ignorance was noticed among patients, with only 10% utilising the correct gland expression technique. It is also notable that 24% of surveyed people based their massage routine on content found on the internet. The hidden need for a device that guides the movement and ensures efficient massage was discovered. It was realised that the provision of an easy to use device would make the patient more confident with eyelid contact and would make the expression of Meibomian Glands an integral part of not only their treatment routine, but also their daily regime Disclosed herein is an eye massage device which is suitable for home or clinic use for a number of therapeutic or cosmetic purposes, and in particular for MGD treatment. As described below the device offers a number of improvements compared to products currently available on the market, in particular for its convenience of use by patients, practitioners and others, its effectiveness, and also ease of manufacture.

Thus in one aspect there is provided a device for massaging one or both of the upper and lower lids of the eye, the device comprising:

a body, which will generally be 'one piece' or 'unitary', being composed of flexible but resilient biocompatible material, wherein the body provides two lips,
wherein the lips are biased into a spaced relationship by the material of the body,
wherein each lip is adapted to engage either the upper or lower eyelid,
whereby, in use, engaging the lips with the upper and lower eyelids and bringing the lips into a proximate relationship causes at least one eyelid to be compressed toward the other.

As explained herein the linear directional massaging movement achievable by the devices of the invention is optimal for expressing meibomian glands.

In preferred embodiments, each lip is the front end surface of a jaw, wherein the body provides:

two jaws, each jaw having a lip, and
the jaws define an orifice, aperture or slot within the body
wherein the two jaws are biased into a spaced relationship by the material of the body,
whereby compressing outer surfaces of the jaws together brings the end surfaces of the jaws (the lips) into the proximate relationship.

The devices described herein are specifically adapted for an optimal interaction with the eyelids and, in particular, bringing the end surfaces of the lips or jaws into a proximate relationship creates a vertical motion on eyelids which causes one or more meibomian glands to be compressed in a direction from peripheral gland to gland orifice causing expression therefrom.

Preferably the device is adapted so that both eyelids are massaged towards each other, but as noted below the device may be narrowed to manipulate fewer numbers of glands, or the lips or jaws may be set closer together to manipulate only part of a gland.

An important element of the present invention is that, in preferred embodiments, it can be adapted or configured so that the lips or end surfaces of the jaws at can be brought together using one hand e.g. with a finger and thumb compressing the outer surfaces of the lips or jaws together.

Preferred embodiments of the device eliminate the complications brought about by the different finger sizes by using the convenient grooves or ridges as described herein, to provide a universal size.

For ease of manufacture the device will generally be formed or constructed from a single biocompatible material, which will generally be an elastomeric material e.g. heat transfer silicon rubber, as explained below.

It will be appreciated that the devices described herein are essentially non-invasive. However biocompatible materials, particular polymers, intended for use in the devices of the present invention can be assessed for suitability using standard USP or ISO testing as required (e.g. USP <88> (biological Reactivity Tests); USP <1031; ISO 10993> (biocompatibility); USP <87> (Cytotoxicity) etc.). Example materials may include synthetic polymers; thermoplastic elastomers; silicone elastomers; styrene block copolymers; thermoplastic copolyesters; thermoplastic polyamides; thermoplastic polyolefins; thermoplastic polyurethanes; thermoplastic vulcanizates etc. Such materials are well known to those skilled in the art and can be selected in the light of the disclosure herein, in particular to provide appropriate resilience, setting properties and so on without undue burden.

As described herein, preferred materials combine one or more of all of the following qualities: safe to be used on the skin and of a medical grade material; right flexibility to allow a compressing action; economical; withstand minimum temperature of 45° C.; durable; able to provide a very good surface finish; compliant with CE marking provisions.

Preferred materials for the present device are silicone materials.

Silicones are synthetic polymeric products made from the natural material silicon.

Silicone Rubber is formed by polymerization of hydroxyl silanes (Simonds et al, 1963). Silicone Rubbers are elastomers and have excellent high temperature resistance and low temperature flexibility (Hamed, 2001 p. 17). Silicones have a relative density of 1.88; Tensile strength of 40 N/mm$^2$; mechanical impact of 0.4 Joules and a maximum service temperature of 450° C. (Higgins, 1977 p. 257).

One preferred material is medical grade silicone rubber with a shore hardness of 22 A and below. This can be confirmed with Shore durometer, which is a handheld instrument pressed into the rubber giving off a measurement displayed at its dial gauge on the scale arbitrary A scale of 0 to 100 (Hamed, 2001 p 317) Medical grade materials can be obtained commercially e.g. from Precision Associates Inc. US (www.PrecisionAssoc.com). Examples include platinum cured and peroxide cured silicone biomedical materials of hardness 35 to 85.

Medical elastomers can be obtained commercially e.g. from Teknorapex, US (http://www.teknorapex.com/division/tpelproducts/medalistl/medalist). Examples include a broad array of thermoplastic elastomer (TPE), thermoplastic rubber (TPR), thermoplastic vulcanizate (TPV), thermoplastic olefin (TPO), and specialty alloy technology solutions. Hardness offerings range from ultrasoft gels at 5 Shore A to hard yet ductile compounds at 85 Shore D.

Yet more medical grade materials which may be applicable to the present invention include Medex 641 extruded styrenic alloy (Prent Corp. Goex Corp).

The device may optionally be hollow. In such embodiments it can be filled with a further substance to modify its physical properties e.g. hardness and resilience e.g. glycerin beads or liquids.

In a preferred aspect of the invention is a device for massaging the upper and/or lower lids of the eye, the device comprising
  a body as described above, wherein the body provides two jaws, which will have an opposing relationship,
  wherein the jaws define an orifice, aperture or slot within the body
  and wherein each jaw has a front end surface
  wherein the two jaws are biased into a spaced relationship by the material of the body
  wherein the end surface of each jaw is adapted to engage either the upper or lower eyelid
  whereby, in use, engaging the end surfaces of the jaws with the upper and lower eyelids and compressing the outer surfaces of the jaws (i.e. the surface facing away from the opposing jaw) together brings the end surfaces of the jaws into a proximate relationship, and thereby causes at least one eyelid to be compressed toward the other In one embodiment the lips or jaws are curved and joined at their sides such to define a body with an essentially ellipsoid longitudinal section. In this embodiment the upper and lower lips or end surfaces together may form an oval which can 'follow' the shape of the eye.

However in preferred embodiments the upper and lower jaws are not directly joined, and may be substantially linear and substantially parallel to one another. In this embodiment there is at least one supporting wall at the rear or sides which connects them, and biases them into the spaced relationship. The wall or walls will be sufficiently stiff or braced to hold the jaws or lips into the appropriate configuration.

Thus in one embodiment the body provides or comprises:
  at least one supporting wall, such that
  the support wall or walls and the inner surfaces of the jaws (i.e. the surface facing towards the opposing jaw) define an orifice within the body.

Preferably there is a supporting wall which is a rear central wall, connecting the jaws together centrally, and distally from the front end surfaces. Where this is the only supporting wall the rear wall and jaws will define a longitudinal channel along the length of the body, and the body will have a generally U- (or C-, the terms are used interchangeable) shaped cross section or profile along its longitudinal axis. The rear wall can act as a fulcrum when bringing the jaws together (or separating them, see below).

The device may include, in addition or in place of a rear wall, one or two side walls connecting the jaws. Where there is one side wall the body will be open at the other side.

In this and other 'open' embodiments (i.e. open at the rear and one or more sides) the void from void from back to front, or side to front, may be usable to apply cream or lotion to the eyelids. Additionally an 'open' conformation makes the device easier to use with a mirror.

In one embodiment there are two supporting walls which are spaced side walls connecting the jaws to define an orifice. Where there are two spaced side walls extending (in the same direction) from the rear base wall, the base wall and supporting side walls define a mouth.

In preferred embodiments the device is slightly elongate so that the lips or jaw end surfaces can engage along the width of a human eye. In preferred embodiments the width of the lips or end surface which engages the eyelids corresponds generally to the distance from the medial canthus to the lateral canthus i.e. the width of the eyelid. However in other embodiments the device may be narrower to permit more massage of more specific areas of the eye, or fewer numbers of glands.

The height defined by the outer surfaces of the jaws or lips at the end surface of the jaws or lips which engages the eyelids may be less than the full size of the extended upper or lower eyelid—for example it may engage only the tarsal plates. A narrow end surface can be used as a 'pincer' and provide increased pressure without excessive skin stretching.

However it may be larger—for example if the device is to be used to massage a lid retraction after ptosis.

In longitudinal section, or profile, the front of the body (through the jaw end surfaces or lips which engage the eyelids) may substantially define:
(i) a square or rectangle
(ii) rounded-corner square or rectangle (or 'squircle')
(iii) an arch having parallel lines on the top and bottom surfaces of the jaws or lips and curvature (e.g. half or quarter circle curvature) at one side and either an open or straight profile at the other side.
(iii) a stadium having parallel lines on the top and bottom surfaces of the jaws or lips and curvature (e.g. half or quarter circle curvature) on the left and right sides.

As explained in more detail below, one or both sides of each end surface or lip may be narrowed or bevelled or otherwise curved, to permit greater accuracy of manipulation of the eyelid, if desired. The end surface may have a non-unifirm or variable height (thickness) to engage the eye in different ways between the canthi—for example it may be thinner at the canthi.

Generally therefore the body, or at least the lips or jaw end surfaces are dimensioned such as to be able to fit onto the eye to engage both eyelids In preferred embodiments the maximum height (i.e. thickness) of each lip or end surface which engages an eyelid is 30 mm, although a narrower thickness is preferred for greater accuracy e.g. between 0.5 and 30 mm e.g. between 3 and 12 mm; between 5 and 10 mm; e.g. about 7, 8, or 9 mm. It will be appreciated, though, that the thickness must be sufficient for the lip or end surface to 'grip' the skin of the outer eyelid when pressed gently against it, bearing in mind also the material from which the lips or end surfaces are composed, and any profiling, shaping or texturing used to improve engagement. However thinner jaws can be used to more accurately manipulate different parts of the glands.

In preferred embodiments the maximum distance height defined by the outer surfaces of the jaws or lips at the end surface of the jaws or lips which engages the eyelids is 40 mm, e.g. less than or equal to 35 mm, e.g. equal to or less than 30 mm, e.g. equal to or less than 25 mm, e.g. equal to or less than less than 20 mm when the body of the device is in its relaxed form (where the lips or end surfaces are biased into a spaced relationship). Preferably the distance is between 30 and 15 mm.

In preferred embodiments the maximum width of the lips or end surface which engages the eyelids is 60 mm e.g. equal to or less than 50 mm, e.g. equal to or less than 40 mm, e.g. equal to or less than less than 30 mm. As described below, quite 'thin' devices e.g. of around 10 mm may be used to more accurately manipulate subsets of glands.

In addition to the basic body of the device, comprising the lips or jaws, and optionally end walls, preferred embodiments may incorporate further structural elements to increase functionality of the device.

For example the device may include ridges or grooves to receive the user's digits. It may include a roughened, textured, tacky or otherwise gripping surface in the areas where it engages the eyelids (lips or end surfaces) or the digits (generally the outer surfaces of the jaws, where they are compressed to achieve the linear massaging action).

The material which engages the lids may have a texture that encourages unidirections movement in the correct massage direction.

Thus, preferably the outer surfaces of the jaws each feature an indentation or concave profile or groove (which may be a longitudinally arranged) for the index finger and the thumb respectively. The concave profile or groove may have a nominal radius of around 10 to 20 mm e.g. 11, 12, 13, 14, 15 or 16 mm and be equal to or at least 3, 4, 5, 6, 7, 8, 9, 10 mm deep. The present inventors have found that such profiles provide an ergonomic and easy to device for a variety of finger sizes. A preferred nominal radius is between 12 and 15 mm and between 3 and 8 mm deep. Alternatively they may include one or two upstanding ridges to achieve the same effect. In an alternative embodiment, the outer surfaces of the jaws each have a pad formed or affixed thereto which is designed and dimensioned to direct where the finger and thumb (or fingers) should compress the surfaces to operate the device. The pads may, for example, be circular or oval such as to be readily 'found' by the tip of the finger or thumb.

Where the device includes a rear or base wall, this may be curved, indented, concave or grooved to accommodate the medium finger. This finger helps to keep the device against the eye, with the appropriate pressure (discussed below).

As previously noted the end surfaces or lips may be bevelled or angled to increase contact with the eyelids. In particular they may be sloped inwards (i.e. in towards the slot, orifice, mouth) so as to facilitate engagement with the eyelids over the convex eye. An example may be approximately 10° slope inwards for each end surface, with respect to the vertical when the device is orientated with the end surfaces facing the eye. The surfaces or lips may be angled to follow the shape of the eye lid i.e. to engage with a sphere of approximate diameter of between 20 and 25 mm.

In another embodiment the jaw end surfaces or lips are provided by cylinders being joined at their rear by a 'U' profiled jaw or supporting base wall. In operating the device the cylinders can roll on the eyelids.

In one embodiment the device includes upstanding lugs, for example upstanding from the outer surface of the jaw or base support wall. Compression of lugs 'opens' the device thereby moving the jaws or lips further apart (a less proximate relationship). This can be useful prior to engaging the eyelids to ensure that they engage with the lids in the desired area. In one embodiment an extended lug may extend longitudinally along back of each jaw. This may be utilised by the thumb In one embodiment the device is actually attached to fingers or thumb to facilitate the operation thereof. For example the jaws may include rear pockets or slots into which the digit(s) can be inserted. In one example there is a separate hoop, ring or channel, attached to the outer surface of the jaws into which the digit(s) can be inserted.

It will be appreciated that the critical features of the device are generally at the front (which engages the eyelids) and outer surfaces of the jaws (top and bottom) which are compressed to achieve the massage action.

In various embodiments the rear of the body may include additional structure to achieve additional functionality. For example the rear of the body (e.g. rear or base supporting wall) may be attached or formed into a handle to help to hold the device. This handle will thus extend in a direction generally away from front end surfaces so as not to interfere with engagement with the eyelids. For example the handle may be designed to be held by the medium, ring and little fingers.

The device (e.g. handle of the device) may include a heating or vibrating mechanism, which will generally include a power source (or could be mains operated). Furthermore, although not preferred, the device may include a mechanism to facilitate compression of the jaws by the user. Vibrating mechanisms may be useful and can be embedded in the handle—these include ultrasound mechanisms.

In addition to the features described herein, other features may be incorporated that are known or believed to give a pleasing feeling of quality in medical devices (Wiklund, 2007; Oppenheimer, 2004). These attributes include: pleasing gripping textures; colours as visual code to assist the user; and avoidance of moulding defects, sharp edges and corners.

In the case of home medical devices for elderly patients, a device that looks too much like a hospital or professional device will convey an undesirable message on the severity of the condition and might impact on the patients' feelings (cetin, 2004) so curved surfaces may be preferred.

The devices of the present invention typically have a unitary body formed from a single piece of biocompatible material. Less preferably they will be formed from two pieces which are attached together.

Thus in another aspect of the invention there is provided a process for producing a device as described above, or the body of such a device, wherein the body is cast as a single piece in mould. Alternatively the body will be cast as two pieces in a mould which are subsequently joined.

In the prototyping described in the Examples below, master models were used to create alginate moulds. Once the alginate congealed, the model was extracted and silicone was cast in the mould.

In a further aspect of the invention, there is disclosed a method for massaging the upper and\or lower lids of the eye, the method comprising:
(i) providing a device as described herein;
(ii) engaging the lips or end surfaces with the upper and lower eyelids; and
(iii) bringing the lips or end surfaces into a proximate relationship,
thereby causing at least one eyelid to be compressed toward the other.

As explained above, the methods of the invention use the device to create a vertical motion on the eyelids which causes one or more meibomian glands to be compressed in a direction from peripheral gland to gland orifice causing compression and expression therefrom.

In preferred methods both eyelids are massaged towards each other but as noted below the device may be narrowed to manipulate fewer numbers of glands, or the lips or jaws may be set closer together to manipulate only part of a gland.

Figure 7:
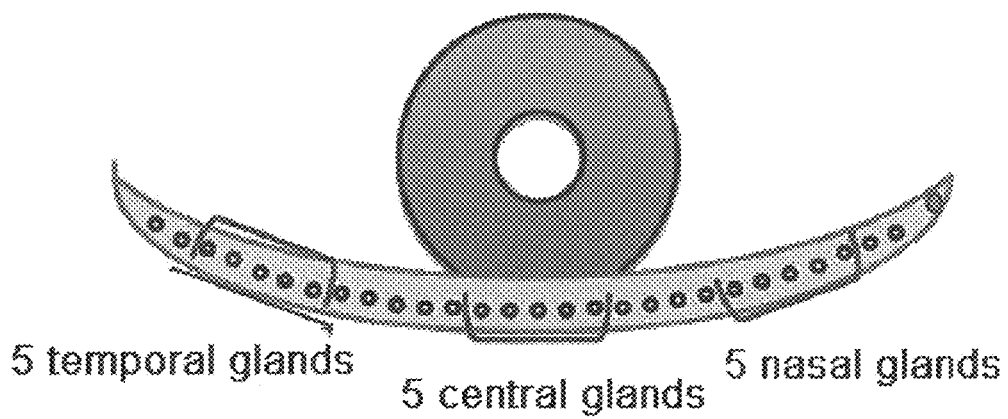

It is known that although the total number of meibomian glands ranges from 50-70, the majority of the active ones are located at the nasal third of the lower eyelid and the least active at the temporal third of the lower eyelid (Korb and Blackie, 2008) as shown in FIG. 7. Thus the method may be directed at manipulating at least the nasal glands, for example.

The lids can be open or closed. When applied to open lids the method may move the lids towards the closed position, with the resistance increasing the pressure or effectiveness of the massage. Where the lids are closed the device can be used to provide an alternative manipulation of the glands, as the jaws or lips are squeezed together.

The preferred motion is vertical and unidirectional i.e. there is no reverse action, and the device is disengaged from the eye after the lips and end surfaces are brought together. The devices and methods are adapted to avoid a 'circular' motion which is less effective at achieving expression from the gland.

Preferably the treatments of the present invention are performed for at least about 10, 11 or 12 minutes. However even shorter treatments (1, 2, 3, 4, or 5 minutes) particularly if repeated at Intervals, may also be of benefit. As explained below, the massage may be used in conjunction with heat treatment.

The preferred method is preferably a manual one, whereby the lips or jaws are closed using any combination of digits on one hand or two e.g. with a finger and thumb of one hand, for example to compress the outer surfaces of the jaws together and apply the desired pressure. Due to the ergonomic design of the device, the massage can be self-administered, although in other embodiments it can be performed by another party.

Preferably the user squeezes the device by placing their fingers and or thumb in grooves or other appropriate conformations (as described above) on the outer surface of the device as explained above.

In some embodiments, as explained above, the device can be attached onto a digit or digits of the user prior to use.

It will be understood that a number of different conformations are possible according to the use required.

The pressure applies against the eyelid using the device will be chosen and self-moderated by the user according to the desired objective of the massage. The pressure may be continuous or intermittent As noted above, and having regard to the structure of the Meibomian glands, massage is most effective when carried out in a vertical motion, towards the lash line, i.e. moving upwards (supraduction) in the lower lid and downwards (infraduction) in the upper lid in order to remove the material from the glands (McMonnies et al., 2012; Driver and Lemp, 1996).

Therapeutic expression will give maximum benefit by applying the maximum pressure tolerated by the patient, usually between 1.0 and 1.4 bars (Tomlinson et al., 2011).

As explained above, the present invention is adapted to massage the eye, and can thus be used as a complement to heat-treatments for the treatment of MGD. The invention addresses the problem identified herein that MGD patients currently suffer from the lack of standardisation of massage and would benefit from a device adapted to give a safe and efficient massage.

Nevertheless it will be understood that the massage device may be used in conjunction with heat treatment, either by use of an integrated heating system (discussed below) or by heating the device with an external source—for example in a microwave oven. Thus in the methods of the invention the device can be heated before or during.

Alternatively the methods may be alternated or otherwise used in conjunction with a separate heat treatment e.g. from a warm compress.

As briefly explained hereinbefore, the rationale for heat stimulation is to liquefy and reduce the viscosity of Meibomian materials. In most cases, a temperature of 40° C. in the glands area is optimal to melt enough material whilst remaining safe (Blackie et al., 2008). In more severe obstructions, higher temperatures may be needed to melt more material (Friedland et al., 2011). Over 40° C., a risk of cornea damage appears (McMonnies et al., 2012). Tear-science® developed a specialised device, LipiFlow®, that can safely reach 42.5° C. to melt more material, but it is more intrusive and requires a specialist to perform the manipulation.

As explained in the Examples, the devices described herein have undergone heating tests with a microwave oven, and were comfortable and pleasant to use when the device was slightly warm (~45° C.). Such a temperature in the device can give near optimal temperatures in the glands themselves.

Although microwave heating is convenient and effective, If desired the device of the present invention may include an electrically powered heat circuit. Such technology is now commonly available, for example in the heated hand gloves use in snow sports.

In one embodiment the device heats up to a temperature of 45° C. maximum, with heating filaments incorporated and heated up by electric power. The device may include an Integrated Chip or Board that is programmed to work at that temperature range incorporating thermal sensors and timers. It may further comprise a switching and charging circuitry to allow recharging of the device via USB or mains supply. The circuitry is thus analogous to that used in commercial rechargeable hand warmers i.e. including a PCB, a rechargeable battery pack to provide the power to a pair of flat hot filaments. In the device of the present invention a thermal sensor can be included to indicate the temperature of the device.

Incorporating a heating element in the device solves some of the limitations encountered in the traditional warm compress. A heating element which is electrically powered can provide a constant heating that can be regulated to suitable temperature e.g. between 32° C. to a maximum of 45° C. Once the maximum temperature is achieved a signal indicator can be triggered to notify the user that the massager is ready to be used. The heating element, or battery pack, may be provided as a separate accessory e.g. in a handle.

The device and methods of the present invention may be used for therapy e.g. prevention, treatment or alleviation of MGD, or injury affect gland function e.g. treatment for dry eye or MGD e.g. a home-treatment of MGD.

Specifically the treatment or prophylaxis may be in respect of any of the symptoms of MGD e.g. red eyes, burning, irritation, itching, fluctuating vision, or inflammation (Driver and Lemp, 1996).

Suitable or individuals for treatment may be those diagnosed according to the TFBUT (Tear Film Break Up Time) e.g. those where their TF breaks in less than six seconds which is at least ten seconds for those with healthy eyes (Butovich, 2011).

Driver and Lemp (1996) suggest that MGD happens more on fair skinned people, living in cooler climates, and that the eyelid performance varies with age. The secretion produced by this glands are said to stabilize at the age of 80 and up (Knop et al 2011). The number of actively secreting meibomian glands tends to decrease by half between the ages of 20 and 80 years, and so the present invention may be of particular benefit to older individuals.

"Prevention" or "prophylaxis" as used herein indicates an action taken at a point in time with the purpose of reducing the likelihood or impact of a future disease or dysfunction, for example by massaging or clearing the glands in order to try and avoid future blockage.

The methods may be performed as part of a regular routine e.g. once or twice daily, for example in the morning and\or evening.

As explained above, the methods and devices, particularly those with an 'open' structure (e.g. void from back to front, or side to front) can be used to apply compositions to the eyelids. This may be for the purpose of applying or distributing drugs, creams, lotions, ointment, drops, slow release chemicals into the skin of the eye lid including meibomian glands, or to the eye surface, or coverings of the eye (conjunctiva, sdear, tenon) and or the eye itself.

Because the device grips the eyelids, it can be used to pull the eyelid away from the eye.

Furthermore it can be applied to the skin surface e.g. bringing wound edges together. Here the force of action brings the wound together. The reverse can be used to treat scars &/or to stretch the skin or a wound on the skin and/or to treat wrinkles. This "opposite action" can be used to treat inverted lids or narrow palpebral apertures.

However the methods of the present invention may also be used for non-therapeutic purposes e.g. massage for comfort purposes.

However the methods of the present invention may also be used for cosmetic purposes. For example the methods may be performed in reverse (i.e. bringing the lips or end surfaces into a more distal relationship, thereby causing at least one eyelid to be compressed away from the other) to treat droopy eyelids or for excess eye lid skin or to prevent skin from drooping over the eyelid. It may also be used to apply cosmetic compositions, as described above.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

FIGURES

FIG. 1. Position and anatomy of the Meibomian glands: Meibomian glands are sebaceous glands named after Heinrich Meibom who defined them in 1666 (Meibom, 1666). Located in the tarsus of the eyelids, they produce an oily secretion (meibum) that covers the tears. The glands are arranged in a parallel formation, perpendicular to the border of the eyelid. They cover the width of the tarsal plate in a single row (Driver and Lemp, 1996; Bron et al., 1997). The length of the glands depends on their location; an average size of 5.5 mm for the upper eyelid and 2.0 mm in the lower eyelid is reported in recent literature (Knop et al., 2011). The number of glands in the upper eyelid is 32±7. There are fewer glands in the lower eyelid, between 20 and 30, but they tend to be wider (Knop et al., 2011). Each gland is actually made of several smaller glands called 'acini', connected to a main canal ('central duct') by smaller canals, the 'ductules'. The structure can be compared to a chain of onions (Bron et al., 1997) or grapes (Driver and Lemp, 1996). The secretion is synthesised in the acini by epithelial cells. The liquid then goes through ductules to reach the central duct. The meibum is delivered to the cornea via the 'excretory duct'. Glands are naturally milked with the contraction of the muscle of Riolan and the pretarsal orbicularis muscle during blinking (Knop et al., 2011; Korb et al., 1994).

Figure 2:
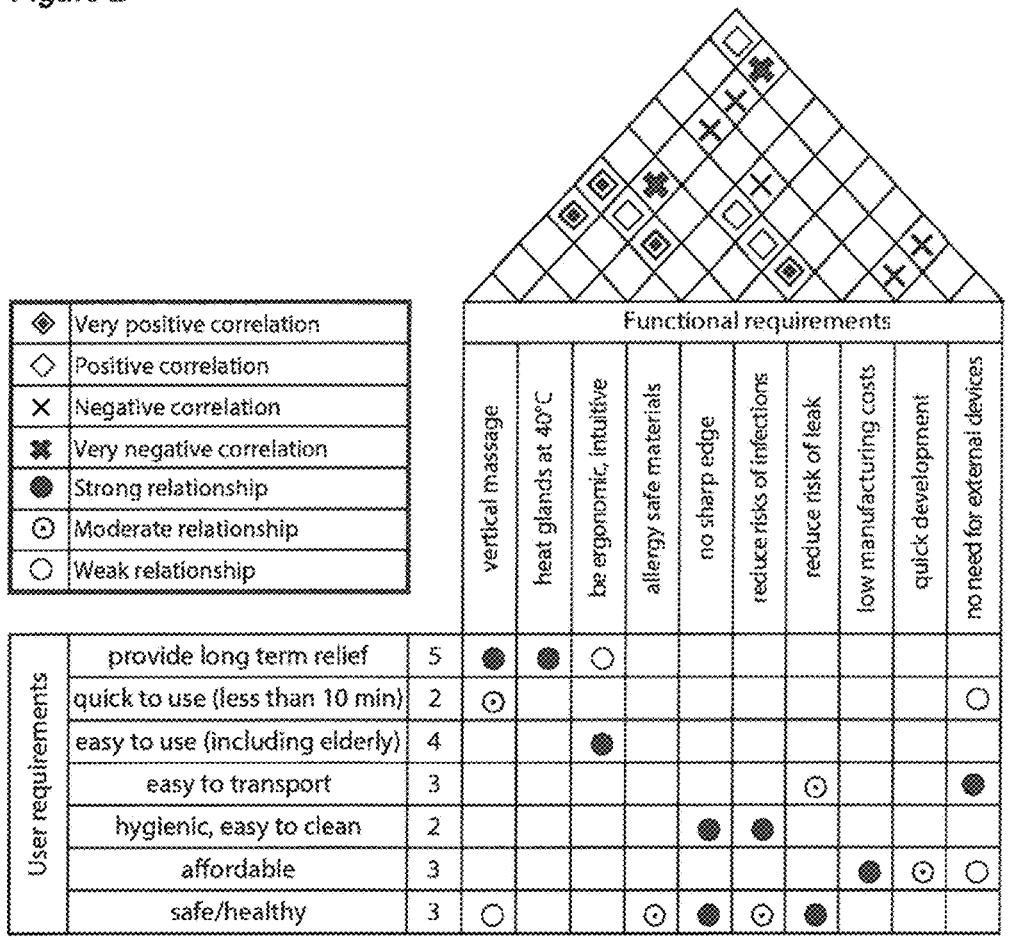

FIG. 2. House of Quality: Users' expectations were gathered from the open question "do you have particular requirements for a new device". Requirements were identified and sorted according to the frequency of answers. A weighting coefficient from 1 to 5 was associated with each requirement, 5 corresponding to the item most frequently cited by respondents. These criteria were used to build a House of Quality for the treatment of MGD FIG. 3. Some shape variations of the eye massager of the present invention.

Figure 4:
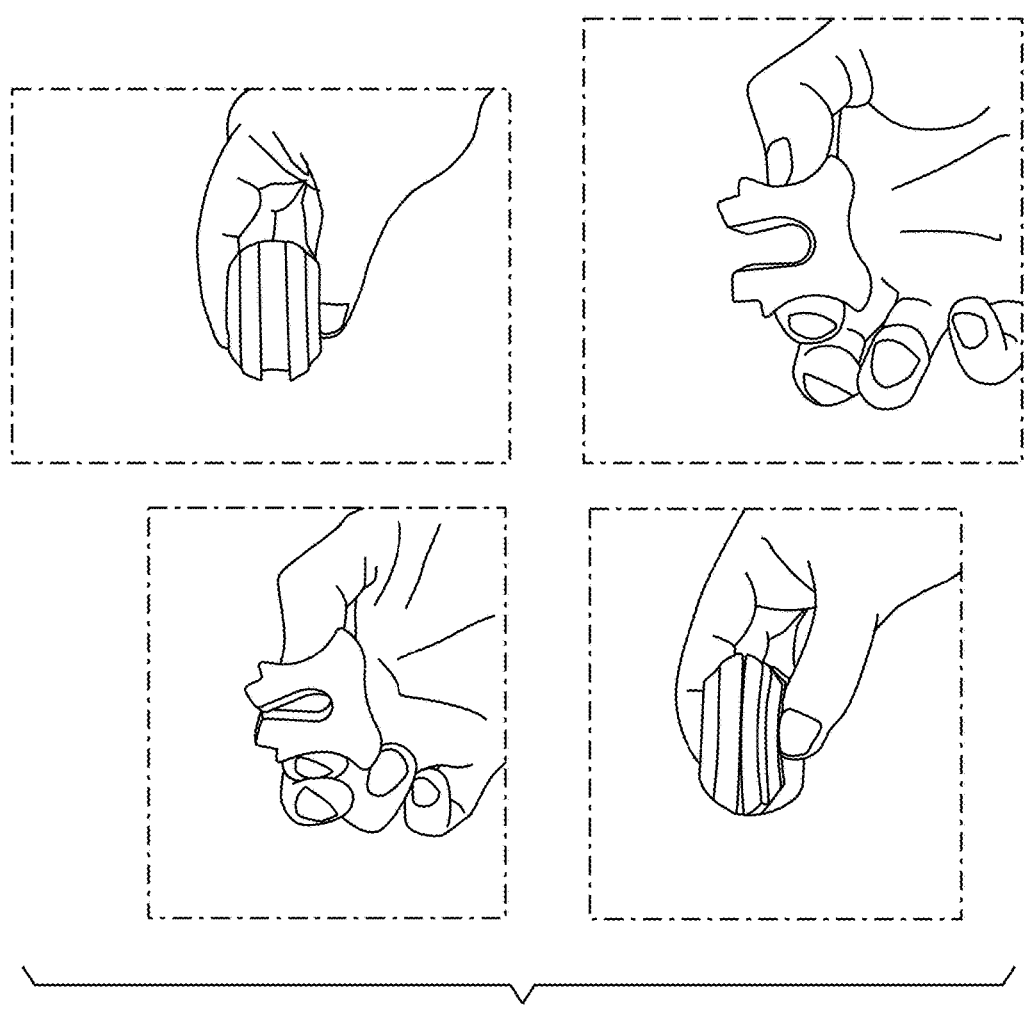

FIG. 4: photos of a preferred embodiment

Figure 5:
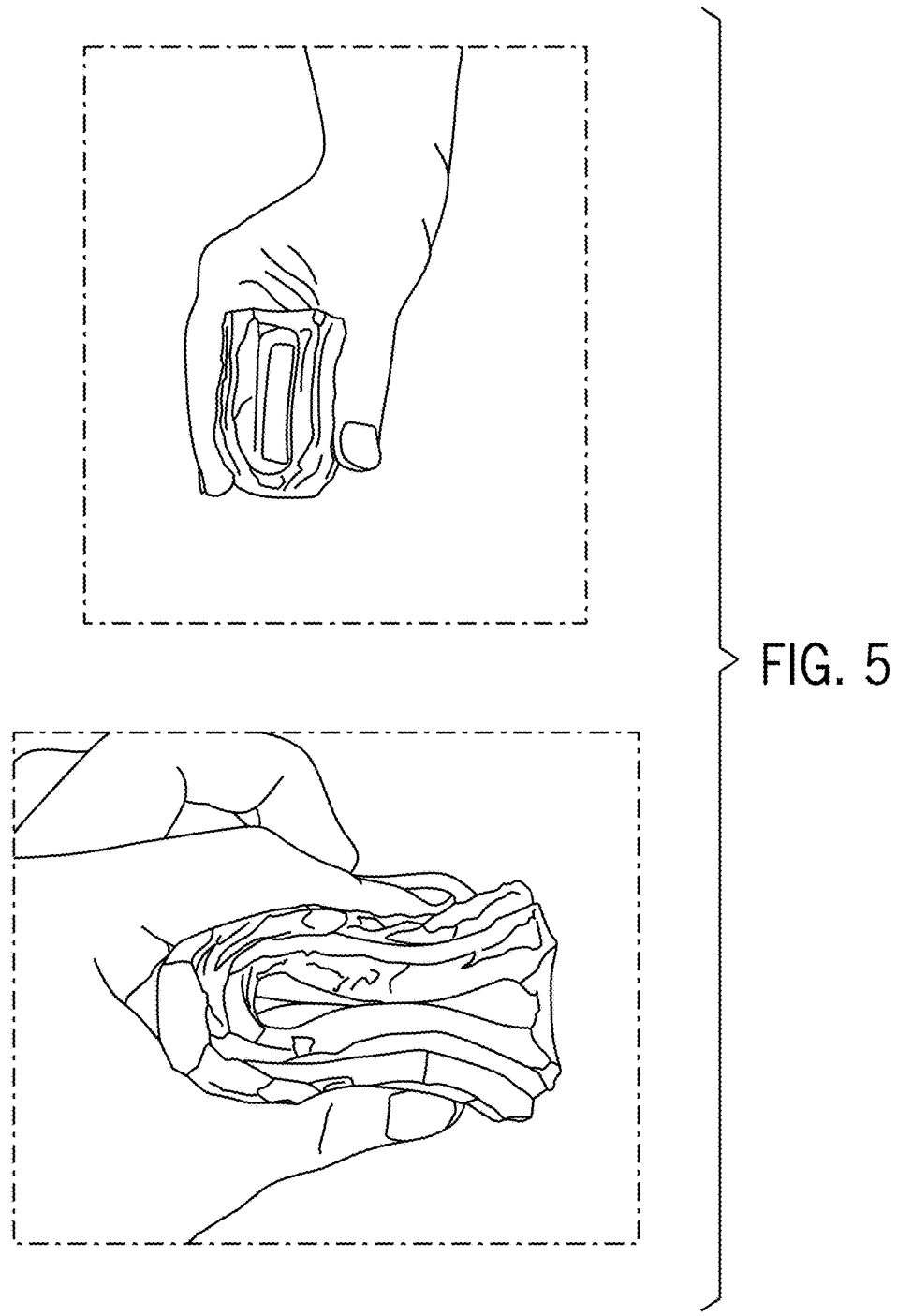

FIG. 5: photos of a further embodiment

FIG. 6a-h: drawings of various embodiments

Figure 6A:
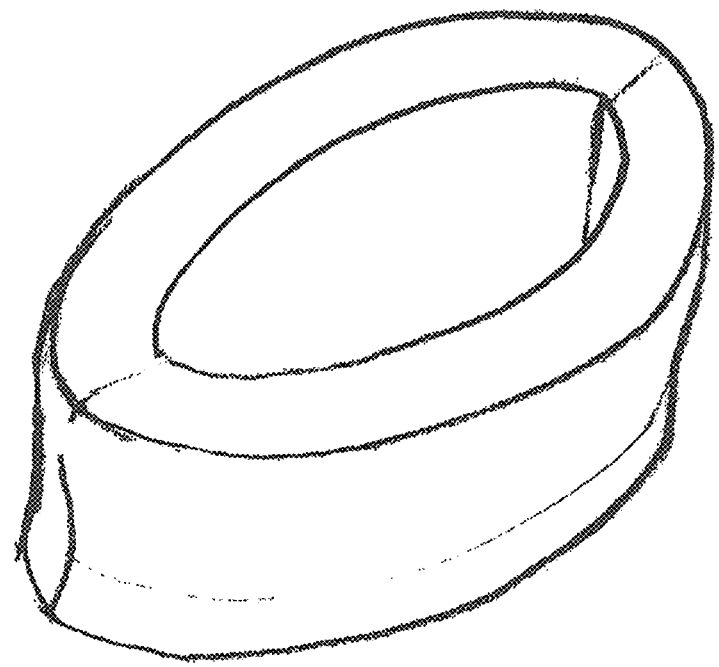

FIG. 6a: Version with closed shape. Usable to apply cream or lotion to the eyelids. The shape follows the eyelids.

Figure 6B:
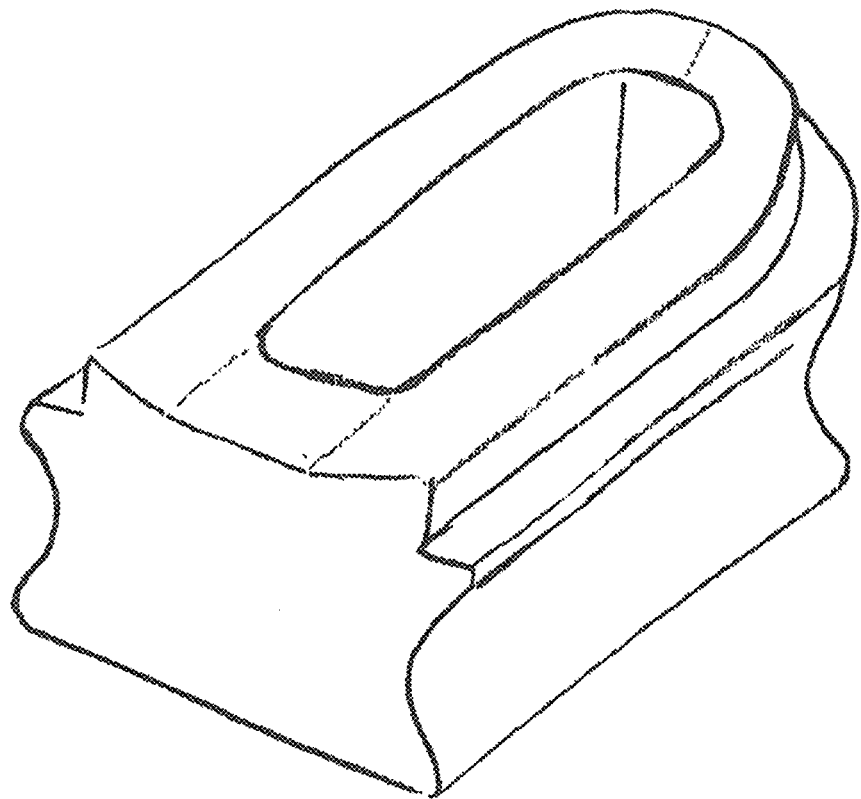

FIG. 6b: Version with dosed shape. Wide grooves accommodate the fingers. The action of squeezing creates a vertical motion on the eyelids. The surface in contact with the eyelids is tilted to provide the best grip.

Figure 6C:
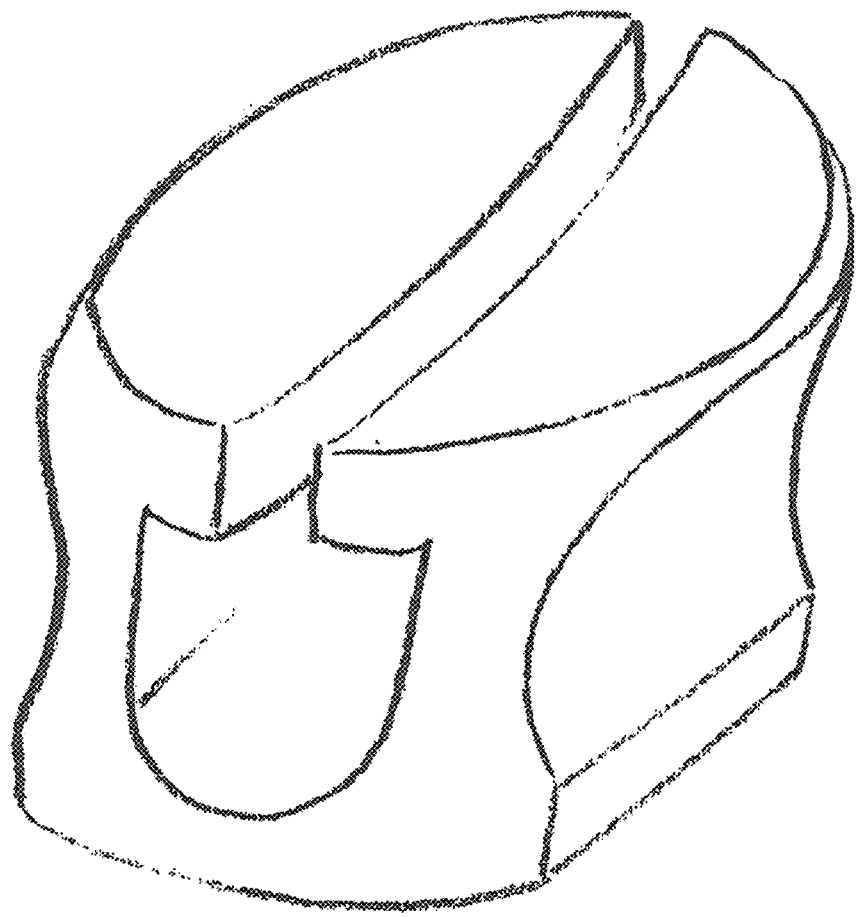

FIG. 6c: The profile is U shaped with a wider surface for the contact with the eyelids. The user squeezes the device by placing his/her fingers in the grooves on the sides.

Figure 6D:
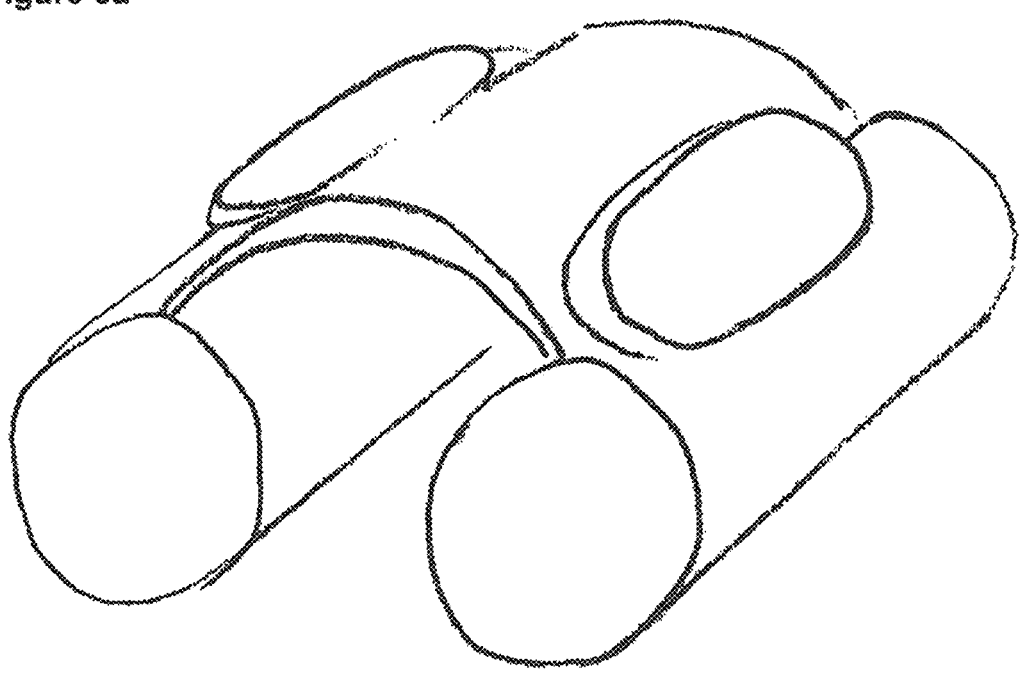

FIG. 6d: The massaging movement is created with two cylinders that roll on the eyelids. The cylinders are linked by a flexible membrane, which gives stiffness to the device.

Figure 6E:
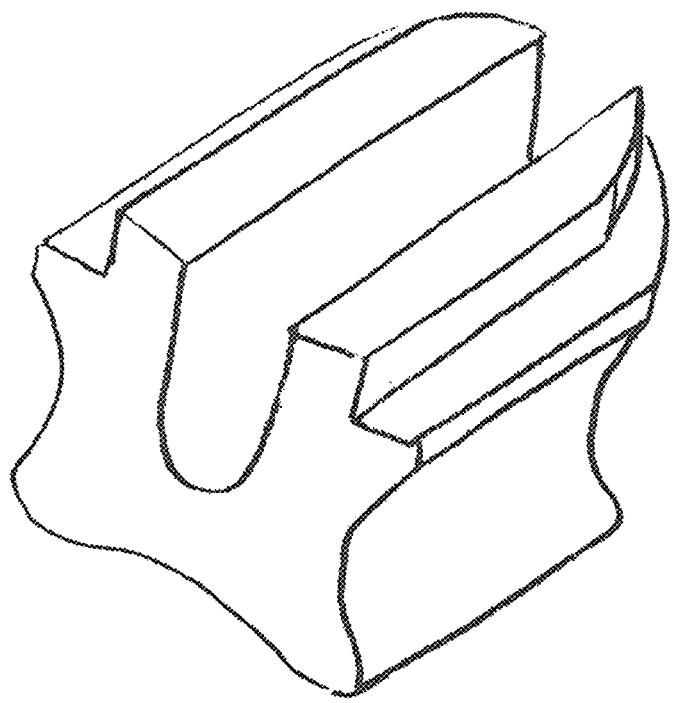

FIG. 6e: Two parallel surfaces are used to grip on the eyelids. The shape is open, which makes it easier to use with a mirror. One side is bevelled to allow more accurate action if desired. The sides feature two deep grooves for the index and the thumb. The back of the device is curved to accommodate the medium finger. This finger helps to keep the device against the eye, with the appropriate pressure.

Figure 6F:
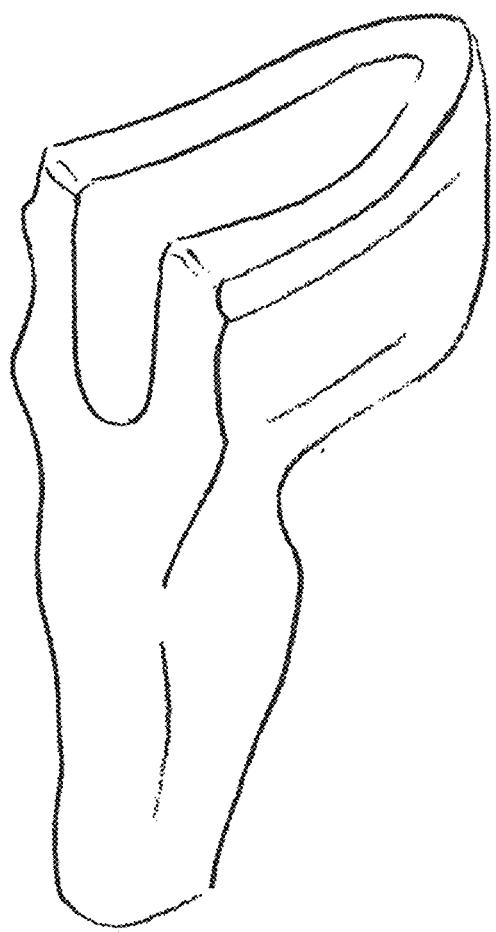

FIG. 6f: This model features a handle to help to hold the object. This handle is designed for the medium, ring and little fingers. The index and thumb squeeze the U shape to provide vertical massage to the Meibomian glands. A heat tank, battery pack for heating elements, and/or a vibrating mechanism can be embedded in the handle.

Figure 6G:
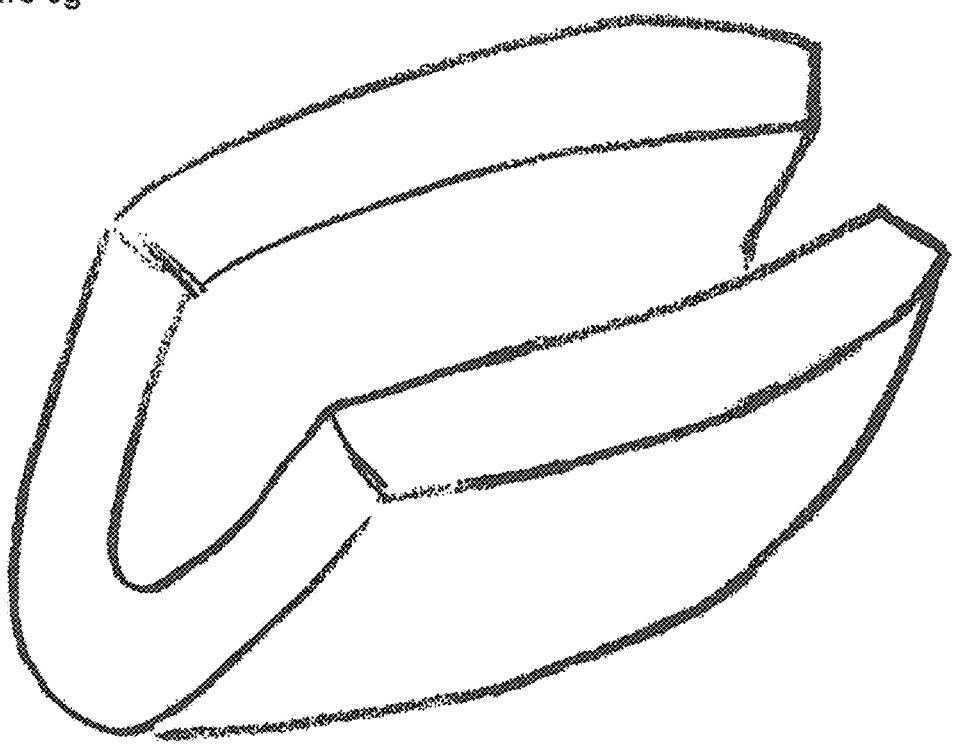

FIG. 6g: A generally U shaped model. The flat surface is applied against the eyelid. The thumb and the index squeeze the device on the sides thus providing a vertical movement that expresses the Meibomian glands.

Figure 6H:
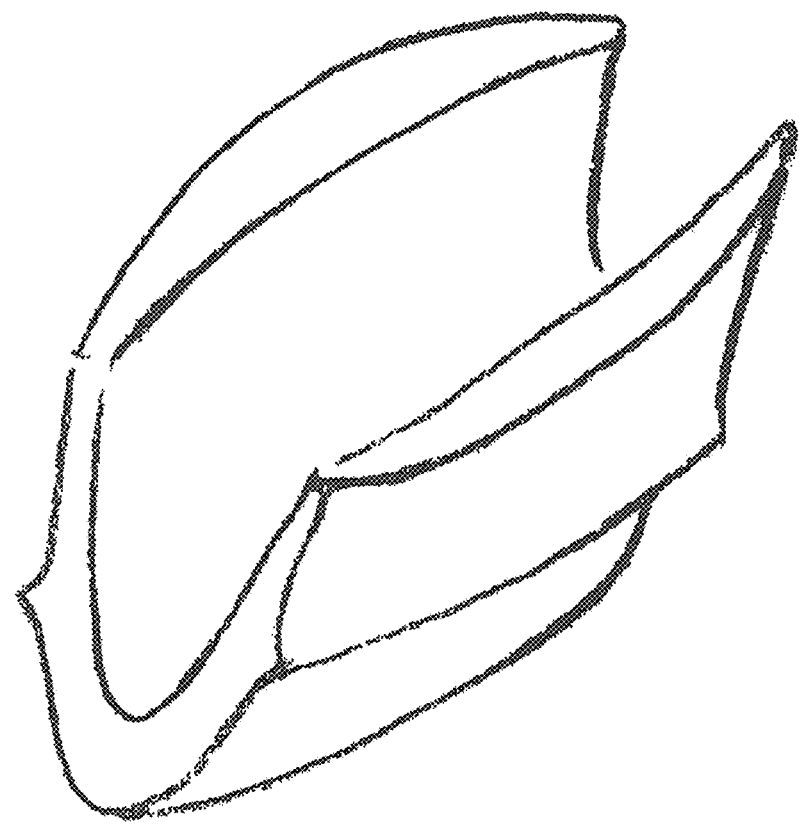

FIG. 6h: A variation of the previous model, more flexible, the surface in contact with the eyelids is narrower. The dents on the sides help to position the fingers.

FIG. 7: The Lower Eye Lid showing the position of the most active nasal glands.

Figure 8:
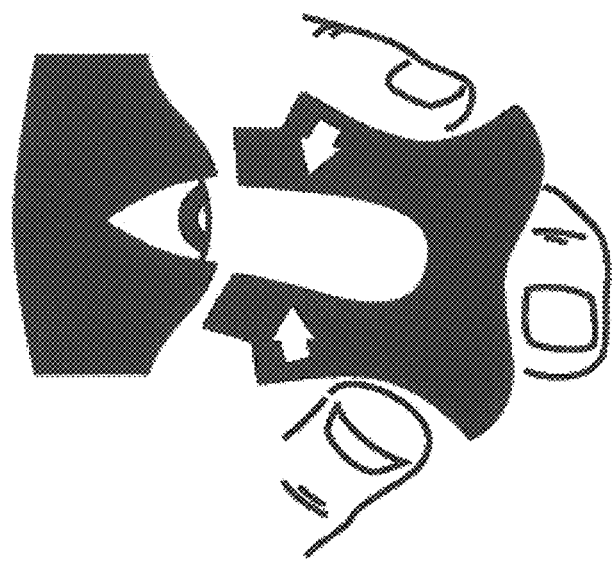

FIG. 8: Schematic figure demonstrating how to use a preferred embodiment of the invention.

Figure 9:
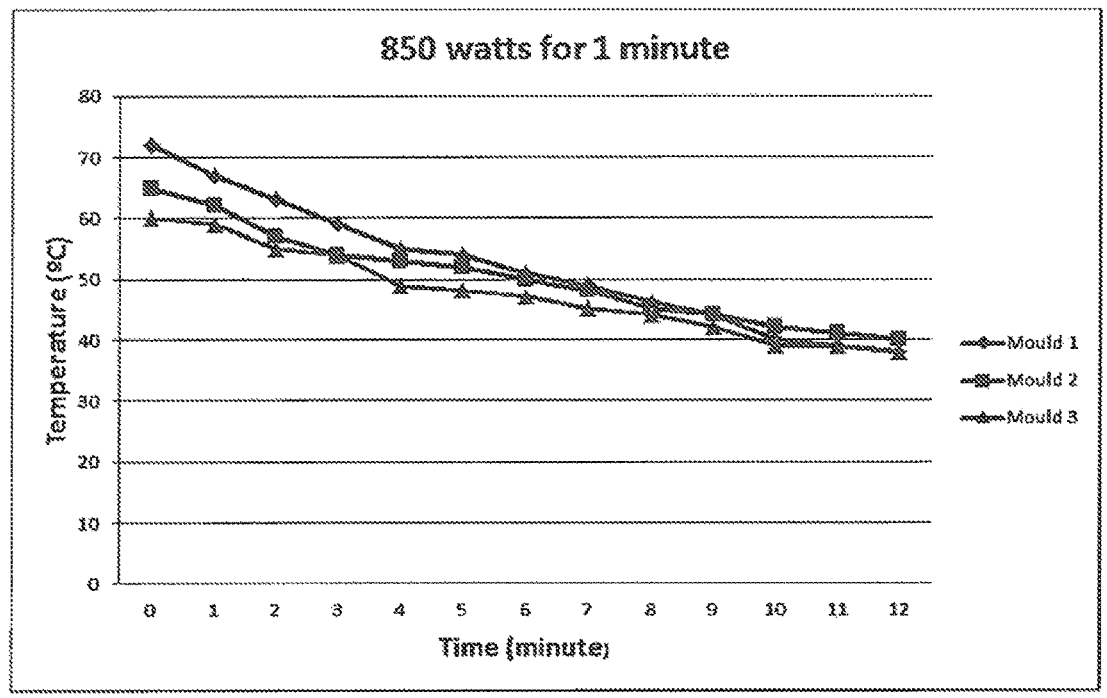
Figure 9:
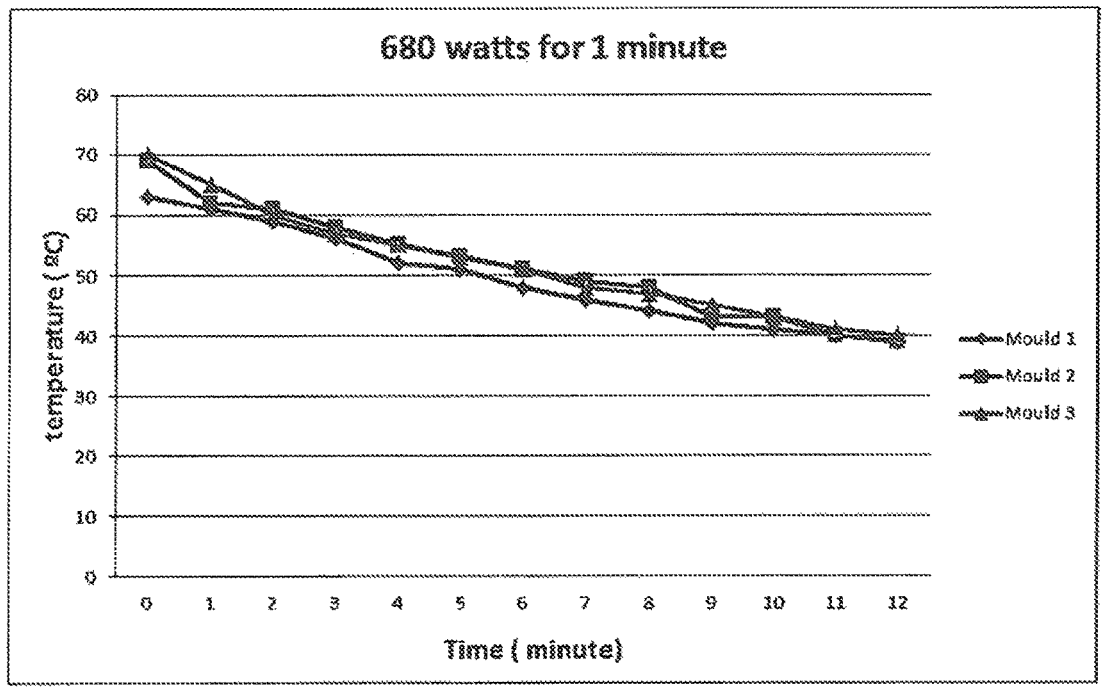
Figure 9:
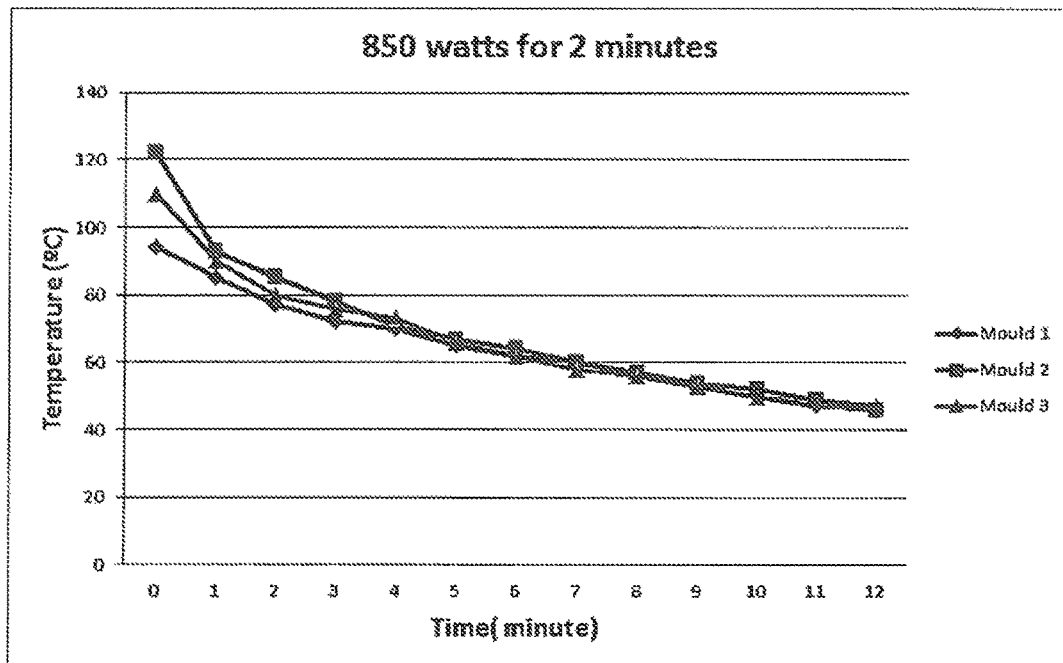
Figure 9:
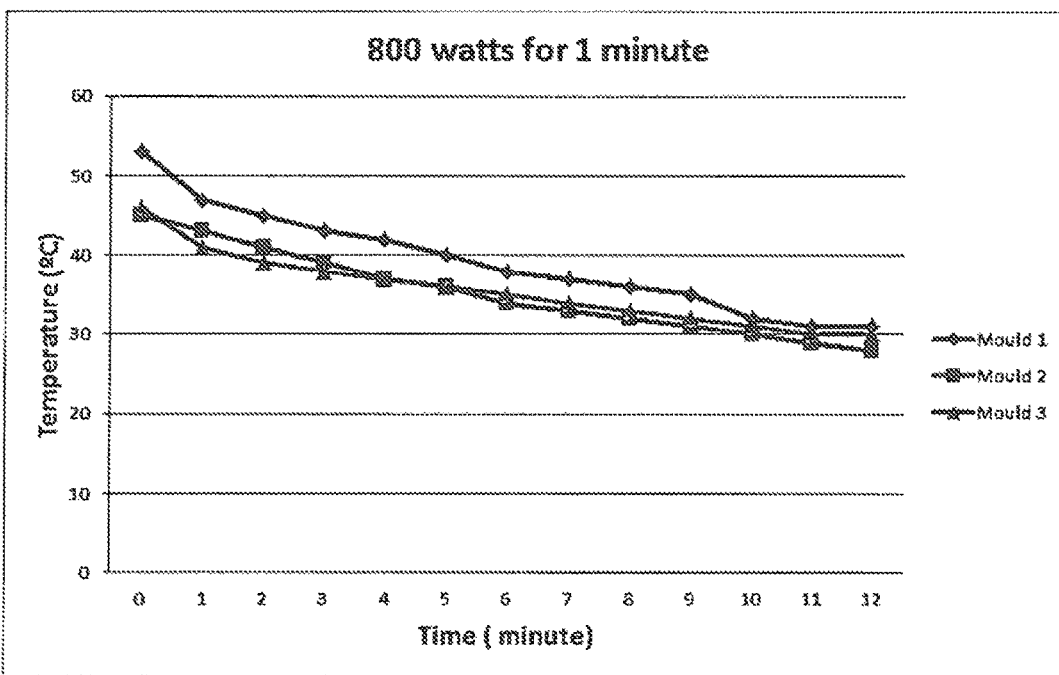

FIG. 9: Results of microwave heating experiments.

FIG. 10: Engineering drawing and dimensions of a preferred embodiment of the invention.

EXAMPLES

Example 1

Background to Design Process

This research has involved interviews with patients suffering from dry eyes syndrome. A sample of four patients was interviewed individually in the clients office. Subjects were asked to describe their routine, and asked to massage their eyes as they do usually. Data was collected on paper forms (Appendix C). A web-questionnaire (Appendix B) posted on the bulletins boards of an online dry eyes community gathered statistics on an international scale. Data was collected with a Google form. Due to its nature, the web survey results must be considered with care: the participants represent a sample of internet users with non-representative awareness of their condition and its treatments. A low risk ethics form was submitted and approved by Cranfield University Ethics Committee prior to conducting any patient research.

The online questionnaire was completed by 138 respondents, 88 of whom suffered from MGD. All the data detailed hereafter is based on MGD patients. Respondents had an average age of 49.7 years (standard deviation: 14.8), were mostly females (76.1%) and the majority lived in the USA (76.1%) or in the EU (13.6%). Overall, participants had been experiencing symptoms during a long period of time, with an average of 9.1 years reported (sd: 8.4). Respondents reported that treatment was carried out on a very frequent basis, with 70% of respondent undertaking treatment several times per day, 22% once a day and 8% not doing treatment on a daily basis. Eye care can happen anytime but predominantly in the morning and in the evening. As shown in Table 3, the time required for the treatment varied mostly from less than 2 minutes to 10 minutes (73% of people). In a separate question, respondents were asked to rate their treatment. Quite logically, quicker treatment time correlated with more satisfied patients. Respondents were asked to describe their massage movement and routine. Results are synthesised in Table 4. It appears that only 10% of respondents massaged their eyes vertically, which was previously identified as the best way to express the glands. A considerable amount of people massage their eyes in an ineffective fashion. By looking at the qualitative data for people that do not massage their eyes, two categories can be identified: those who tried massage but without significant results, and those who were advised not to touch their eyes because of irritations or recent surgery. The results were connected with the way the person had been taught massage in Table 5.

TABLE 3

| | Time spent on the treatment | | | | |
|---|---|---|---|---|---|
| | <2 min | 2-5 min | 5-10 min | 10-15 min | >15 min |
| Respondents | 23 | 17 | 24 | 11 | 12 |
| Percentage | 28% | 20% | 28% | 13% | 14% |
| Duration average mask (0 to 5) | 4.0 | 3.6 | 3.0 | 3.0 | 2.3 |

TABLE 4

| | Methods of massage and their adoption by respondents | | | | | | |
|---|---|---|---|---|---|---|---|
| | Vertical | Circular | Horizontal | Pressure | Other | No regular massage | Total |
| Amount | 9 | 11 | 8 | 9 | 13 | 37 | 87 |
| Percentage | 10% | 13% | 9% | 10% | 15% | 43% | 100% |

TABLE 5

| | Massage education | | | | | |
|---|---|---|---|---|---|---|
| Recommended by | Percentage of total | Vertical | Circular | Horizontal | Pressure | Other |
| Doctor | 44% | 4 | 4 | 3 | 4 | 7 |
| Internet | 20% | 3 | 1 | 3 | 2 | 1 |
| Nobody | 24% | 1 | 5 | 1 | 2 | 3 |
| Combination | 12% | 1 | 1 | 1 | 1 | 2 |

Doctors are the main source of knowledge. It is notable that some doctors recommend carrying out a circular or horizontal motion, although that has little effect on the glands. A significant number of respondents learnt to massage by consulting websites or online videos. This finding can be explained in part by the target audience of the questionnaire and by the lack of information on the subject. It is likely to be much smaller on a representative sample of patients. Nearly a quarter of respondents reported that nobody really told them to massage. A relative ignorance of massage techniques can be deduced from this study. Patient interviews and observations enabled the collection of more qualitative data. Patients were asked to perform an eye massage. Observations confirmed the questionnaire findings. New insights were also obtained, for example, patients pointed out that temperature control is inaccurate with microwave ovens. Some masks tend to burst if they stay too long or under inadequate power in the oven. When travelling, it is not always possible to heat the mask, which prevents patients from carrying out the treatment. The questionnaire showed potential acceptance of using an electrical device: 96% would not be against the use of a mains powered device.

A House of Quality for the treatment of MGD is displayed in FIG. 2. Four negative correlations are associated with embedded heating. This feature would make the device considerably more complex and more expensive, with a longer development phase. A trade-off could be to achieve heating using a separate device, for example a heat mask widely available on the market.

Example 2

Prototyping

The prototyping phase intrinsically embeds a proof-of-concept that helps to assess the feasibility of the idea. As described by Tjalve (1979), 'graphical' variations are an important step of industrial design. In the scope of this project, real object variations were easily achieved thanks to prototyping materials. Shapes were obtained utilising craftsmanship prototyping processes. Master plasticine models were used to create alginate moulds (mixing Ratio for fast set alginate: 1 part alginate to 4 parts water, mix vigorously for 90 seconds and let it set for 5 minutes: (scarva.com, 2012))

After the alginate mould was prepared it was poured into a plastic tub and then the plasticine model was then submerged to get the negative of the mould. When the alginate has set properly in 5 minutes the mould was then cut in half to take out the plasticine mould inside.

The silicone mixture is then prepared for this concept the mixing ratio are as below:
60 grams base silicone; 6 grams catalyst; 1 gram silicone blue colour pigment.

The mixing ratio was calculated using the mixing ratios provided by the silicone manufacturer at scarva.com.

This silicone was then injected into the alginate mould and left to set for at least 6 hours. Silicone prototypes were unmoulded 24 hours later and deburred with a razor blade.

So-called "Concept A" was selected because of its simplicity, the absence of moving mechanical parts and its small size that make it easy to carry in, for example, a handbag.

Figure 3:
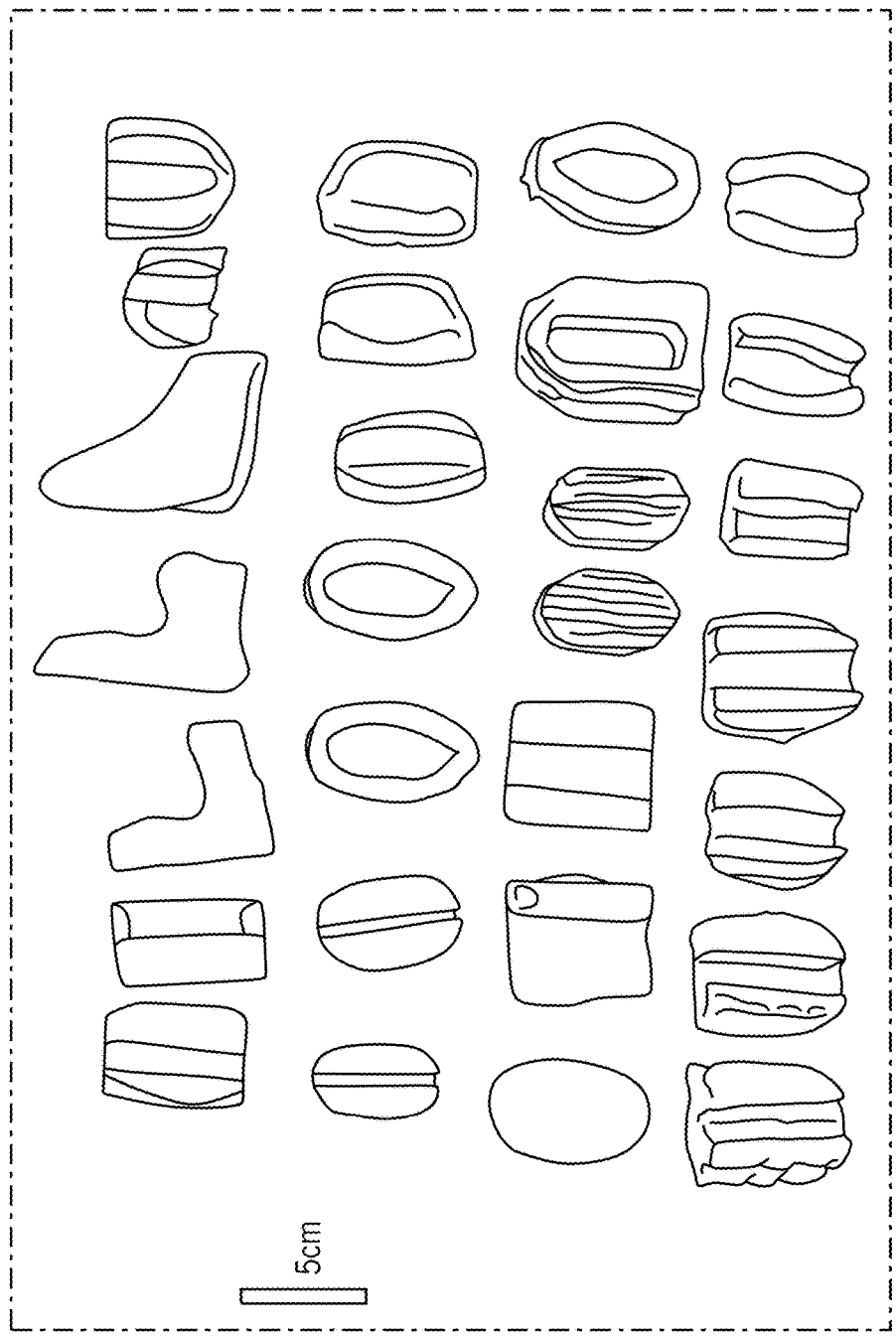

More than 30 different shape variations of the amended Concept A were made (FIG. 3). Observation of the behaviour of the device when squeezed acted as a natural selection and enabled early elimination of several concepts, to create time to focus on the most efficient ones. Various materials and surface roughness were benchmarked according their grip on the eyelid skin and stiffness when squeezing.

After a few cycles of prototyping and testing, the best shape was determined. It was 3D modelled with Solid-Works®. A two-part mould was engineered to reduce the formation of bubbles during the casting process and to ensure that no potential defects were apparent in the surface of contact with the eye lids. Selective Laser Sintering (SLS) was used to rapid prototype the mould in nylon. The model can be used to cast silicone and thus replicate a limited series of the object.

Ergonomics specialists confirmed that large grooves for the fingers are features that make the use of the device more intuitive and limit the risk of misuse.

The prototypes underwent some heating tests with a microwave oven. The silicone used resists to temperatures over 150° C. The device turned out to be comfortable and very pleasant to use when slightly warm (~45° C.). This statement was confirmed by ophthalmologists.

Example 3

Detailed Description of Preferred Embodiment

Engineering drawing showing the dimensions are shown in FIG. 10.

The prototyping process resulted in simplification of the device design, better usability and a number of shapes that offered the right proportions to fit comfortably on the eye.

In the preferred embodiment, and regarding ergonomics, the choice of intuitive large grooves to accommodate the fingers made the device more obvious and easier to use. This feature is also useful for elderly people that may lack dexterity in their fingers. A graphical aid engraved on top of the device would help the user to understand where to position the tool on the eye.

Use of the Device

FIG. 8 illustrates the way the massage is done using the preferred embodiment, with the index and fore finger at the sides of the device and the middle finger at the bottom for support.

In tests, the device was applied against the eyelids of a person with meibomian gland dysfunction and the lids massaged. The meibomian glands were milked and the sebum could be seen to be expressed as expected from the gland orificies. The person felt comfort after the massage. Warming the device for 30 seconds in the microwave improved the comfort when reapplied to the eyelids and the eyelids massaged.

Surface Roughness Analysis

Surface roughness was assessed using a Talysurf CCI Lite 3D Profiler.

Measurements were taken from the part of the prototype device which touched the eye lids. The results are as follows:

| Parameters calculated on the surface Silicone prototype00003 > . . . > Waviness, Gaussian Filter, 8 µm Sz, Sds and Ssc parameters are defined according to EUR15178N report. | |
|---|---|
| Amplitude Parameters | |
| Sq = | 1.1 µm |
| Sa = | 0.884 µm |
| Sp = | 4.27 µm |
| Sv = | 3.93 µm |
| St = | 8.21 µm |
| Ssk = | −0.258 µm |
| Sku = | 3.18 µm |
| Sz = | 6.04 µm |
| Hybrid Parameters | |
| Sdr = | ***** |

Sdr: Developed Interfacial Area Ratio.

Heating Assessment

Tests below were done in order to observe the temperature of the mould when heated using the microwave and how long a suitable temperature can be achieved. These tests will also try to subject the mould with the highest possible temperature to perform a destructive test.

Two kinds of microwave oven were used with different brands, dimensions and power specifications. The power rating was varied and time the mould was inside the microwave. Three moulds were made to be used for this experimental work to allow the other moulds to cool down before they are used for the next measurement. An infrared thermometer was used to measure the temperatures of the moulds for greater accuracy.

Equipment Used (Specifications Taken from Respective Operations Manual):
Microwave 1
Model: LG MS2549DR
Power Input: 230V AC, 50 Hz
Output: 850 W
Microwave Frequency: 2450 MHz
Power Consumption: 1250 W
Outside dimensions: 507(W)×283(H)×435 (D) mm
Microwave 2
Model: Sharp R-270
Power Input: 230-240V AC, 50 Hz
Power Consumption: 1200 W
Output: 850 W
Microwave Frequency: 2450 MHz
Outside dimensions: 450(W)×262(H)×342 (D) mm
Infrared Thermometer
Model: RS 1327 Remote Temperature Measurement (Non-Contact)
Output <1 mW wavelength 630-670 nm class (II) laser product; Electrical specifications can be found in Appendix J.
Emissivity Value Used: 0.9

The microwave heating experiment identified the time taken for the device to heat up to a suitable temperature, and also to observe what temperatures causes visible damage to the device.

From FIG. 9 it can be seen that a suitable temperature can be rapidly obtained, and can be achieved at for several minutes, thus allowing the user to perform the massage with the heat applied.

Where higher temperatures were used visible deformation was noticed and the mould bowed out but regained its original shape after 2 minutes outside of the microwave oven.

REFERENCES

Andreasen, M. M. (2011), "45 Years with design methodology", Journal of Engineering Design, vol. 22, no. 5, pp. 293-332.

Asfour, S., Iakovou, E. and Cortes, G. A. (1999), "A synthesis of quality function deployment and robust design and its application in the medical device industry", Quality Engineering, vol. 12, no. 1, pp. 37-45.

Bitterman, N. (2011), "Design of medical devices—A home perspective", European journal of internal medicine, vol. 22, no. 1, pp. 39-42.

Blackie, C. A., Solomon, J. D., Greiner, J. V., Holmes, M. and Korb, D. R. (2008), "Inner eyelid surface temperature as a function of warm compress methodology", Optometry and Vision Science, vol. 85, no. 8, pp. 675-683.

Bolton, S. (Professor), (2011), Customer Lifestyle Engineering (unpublished lecture at Cranfield University), Cranfield, UK.

Bron, A. J., Tripathi, D. M. and Tripathi, B. J. (1997), Wolff's Anatomy of the Eye and Orbit, 8th ed, Chapman & Hall Medical, London.

Bron, A. J., Tiffany, J. M., Gouveia, S. M., Yokoi, N. and Voon, L. W. (2004), "Functional aspects of the tear film lipid layer", Experimental eye research, vol. 78, no. 3, pp. 347-360.

Butovich, I. A. (2011), "Lipidomics of human Meibomian gland secretions: Chemistry, biophysics, and physiological role of Meibomian lipids", Progress in Lipid Research, vol. 50, pp. 278-301.

Çetin, A. (2004), Applying Product Design Methods to Medical Devices Design with a Case Study on Home Care Devices (Master of Industrial Design thesis), Izmir Institute of Technology, Izmir, Turkey.

Cooper, R. G. (1990), "Stage-gate systems: A new tool for managing new products", Business horizons, vol. 33, no. 3, pp. 44-54.

Den, S., Shimizu, K., Ikeda, T., Tsubota, K., Shimmura, S. and Shimazaki, J. (2006), "Association between meibomian gland changes and aging, sex, or tear function", Cornea, vol. 25, no. 6, pp. 651-655.

Driver, P. J. and Lemp, M. A. (1996), "Meibomian Gland Dysfunction", Survey of Ophthalmology, vol. 40, no. 5, pp. 343-367.

Forlizzi, J., Hirsch, T., Hyder, E. and Goetz, J. (2001), Designing Pleasurable Technology for Elders, INCLUDE, International Conference on Inclusive Design and Communications, London, England.

Friedland, B. R., Fleming, C. P., Blackie, C. A. and Korb, D. R. (2011), "A novel thermodynamic treatment for meibomian gland dysfunction", Current eye research, vol. 36, no. 2, pp. 79-87.

Fries, R. C. (2001), Hand book of Medical Device design, Marcel Dekker, New York.

Gillier, T., Piat, G., Roussel, B. and Truchot, P. (2010), "Managing innovation fields in a cross-industry exploratory partnership with C-K design theory", Journal of Product Innovation Management, vol. 27, no. 6, pp. 883-896.

Glenn, M. (1993), "Quality function deployment for a medical device", Anon (ed.), in: IEEE Symposium on Computer-Based Medical Systems, 13 Jun. 1993 through 16 Jun. 1993, Ann Arbor, Mich., USA, Publ by IEEE, Piscataway, N.J., United States, pp. 10.

Gutgesell, V. J., Stem, G. A. and Hood, C. I. (1982), "Histopathology of meibomian gland dysfunction", American Journal of Ophthalmology, vol. 94, no. 3, pp. 383-387.

Hamed, G. R. (2001), "aterials and Compounds", in: Gent, A. (editor), Engineering with Rubber. How to Design Rubber Components, 2nd edition, HanserGardner Publications, p. 1-34.

Hatchuel, A. and Weil, B., (2002), La théorie C-K: Fondements et usages d'une théorie unifiee de la conception, Colloque <<Sciences de la conception>> ed., Lyon.

Higgins R. A. (1977), Properties of Engineering Materials, Robert E. Krieger publishing company, Huntington New York.

Hom, M. M., Martinson, J. R., Knapp, L. L. and Paugh, J. R. (1990), "Prevalence of Meibomian gland dysfunction", Optometry & Vision Science, vol. 67, no. 9, pp. 710-712.

Howard, T. J., Culley, S. J. and Dekoninck, E. (2008), "Describing the creative design process by the integration of engineering design and cognitive psychology literature", Design Studies, vol. 29, no. 2, pp. 160-180.

Howarth, P. (Opthalmologist and Ergonomist), (2012), Interview the Aug. 14, 2012 at Loughborough University (unpublished interview), Lougborough, UK.

Hykin, P. G. and Bron, A. J. (1992), "Age-related morphological changes in lid margin and meibomian gland anatomy", Cornea, vol. 11, no. 4, pp. 334-342.

Jester, J. V., Nicolaides, N. and Smith, R. E. (1981), "Meibomian gland studies: histologic and ultrastructural investigations", Invest. Ophthalmol. Vis. Sci, vol. 20, no. 4, pp. 537-547.

Knop, E., Knop, N., Millar, T., Obata, H. and Sullivan, D. A. (2011), "The International Workshop on Meibomian Gland Dysfunction: Report of the Subcommittee on Anatomy, Physiology, and Pathophysiology of the Meibomian Gland", Investigative Ophthalmology & Visual Science, vol. 52, no. 4, pp. 1938-1969.

Korb, D. R., Baron, D. F., Herman, J. P., Finnemore, V. M., Exford, J. M., Hermosa, J. L., Leahy, C. D., Glonek, T. and Greiner, J. V. (1994), "Tear film lipid layer thickness as a function of blinking", Cornea, vol. 13, no. 4, pp. 354-359.

McMonnies, C. W., Korb, D. R. and Blackie, C. A. (2012), "The role of heat in rubbing and massage-related corneal deformation", Contact Lens and Anterior Eye.

MDD93/42/ECC "Concil directive of 14 Jun. 1993 concerning medical devices" Official Journal L 169, Jul. 7, 1993 P. 0001-0043 Meibom, H. (1666), De Vasis Palpebrarum Novis Epistola Helmestadi: Typis & sumptibus. Henningi Mulled, Helmstadt, Germany.

Mudgil, P. and Millar, T. J. (2011), "Surfactant properties of human meibomian lipids", Investigative Ophthalmology and Visual Science, vol. 52, no. 3, pp. 1661-1670.

Norman, D. A. (2004), Emotional Design—why we love (or hate) everyday things, Basic Books, New York, USA.

Nom, M. S. (1979), "Semiquantitative interference study of fatty layer of precorneal film", Acta Ophthalmologica, vol. 57, no. 5, pp. 766-774.

Ong, B. L. and Larke, J. R. (1990), "Meibomian gland dysfunction: some clinical, biochemical and physical observations.", Ophthalmic Physiol Opt, vol. 10, no. 2, pp. 144-148.

Oppenheimer, A. (2004), "New considerations for medical appliance designers", Appliance, vol. 61, no. 8, pp. 44-45.

Plattner, H. (2010), "Bootcamp Bootleg" Institute of design of Stanford, Stanford, Calif., USA. http://dschool.stanford.edulwp-contentluploads/2011/03/BootcampBootleg2010v2SLIM.pdf—accessed September 2012

Schaumberg, D. A., Nichols, J. J., Papas, E. B., Tong, L., Uchino, M. and Nichols, K. K. (2011), "The International Workshop on Meibomian Gland Dysfunction: Report of the Subcommittee on the Epidemiology of, and Associated Risk Factors for, MGD", IOVS, Special Issue, vol. 52, no. 4.

Sharma, A. and Moore, J. (Opthalmologists), (2012), Several interviews between May and September 2012 (unpublished interviews), Bedford, UK.

Simonds, H. R. and Church, J. M., (1963), A concise guide to plastics, $2_{nd}$ ed, Reinhold publishing corp, New York.

Schein, O.D., Mufloz, B., Tielsch, J. M., BandeenRoche, K. and West, S. (1997) "Prevalence of dry eye among the elderly" American Journal of Ophthalmology, vol. 124, no. 6, pp. 723-728.

Shimazaki, J., Sakata, M. and Tsubota, K. (1995), "Ocular surface changes and discomfort in patients with meibomian gland dysfunction", Arch Ophthalmol, vol. 113, pp. 1266-1270.

Summerhayes, K. and Sivshankar, S., (2006), The Challenges of Conductiong Medical Devices Studies, ICR Publishinng, Marlow, UK.

Terada, O., Chiba, K., Senoo, T. and Obara, Y. (2004), "Ocular surface temperature of meibomia gland dysfunction patients and the melting point of meibomian gland secretions", Nippon Ganka Gakkai zasshi, vol. 108, no. 11, pp. 690-693.

Tjalve, E. (1979), Engineering graphic modelling: a workbook for design engineers, Newnes-Butterworths, London.

Tomlinson, A., Bron, A. J., Korb, D. R., Amano, S., Paugh, J. R., Pearce, I., Yee, R., Yokoi, N., Arita, R. and Dogru, M. (2011), "The International Workshop on Meibomian Gland Dysfunction: Report of the Diagnosis Subcommittee", IOVS, Special Issue, vol. 52, no. 4, pp. 2006-2049.

Tu, N., Zhang, T., He, Q., Zhang, H. and Li, Y. (2011), "User-centered design in new product development: A case study in developing new sports earphone", 2011 International Conference on Computer and Management, CAMAN 2011.

USADoD (United States Department of Defense) (2011) Technology Readiness Assessment (TRA) Guidance Wiklund, M. (2007), "Refined touchpoints drive quality perceptions", Medical Device and Diagnostic Industry, vol. 29. no. 11, pp. 56-61.

The invention claimed is:

1. A device for massaging both upper and lower eyelids, the device comprising:
a body, composed of flexible resilient biocompatible material,
two jaws, which have an opposing relationship,
wherein the jaws define an orifice, aperture or slot within the body,
and wherein each jaw has a front end surface,
and wherein the two jaws are biased into a spaced relationship by the material of the body, and wherein the front end surface of each jaw is adapted to engage either the upper or lower eyelid,
such that movement of each front end surface causes movement of at least one of the upper and lower eyelids with respect to the other eyelid, whereby, in use, manually engaging the front end surfaces of the jaws with the upper and lower eyelids and manually compressing outer surfaces of the jaws together brings the front end surfaces of the jaws into a proximate relationship, and thereby causes at least one eyelid to be compressed toward the other in a linear directional movement which causes one or more meibomian glands to be compressed in a direction from peripheral gland to gland orifice for expression of sebum therefrom, wherein the device is adapted so that the front end surfaces are brought together using one hand or two hands of a user,
wherein the body's upper and/or lower outer surfaces incorporate an indentation or concave profile or groove to receive digits of the user, to facilitate compression of the front end surfaces together.

2. A device as claimed in claim 1 wherein the jaws are substantially linear and substantially parallel to one another, wherein the device comprises at least one supporting wall at the device's rear or sides which connects the jaws and biases the jaws into the spaced relationship.

3. A device as claimed in claim 2 wherein the at least one supporting wall and inner surfaces of the jaws define an orifice within the body.

4. A device as claimed in claim 3 wherein the at least one supporting wall is a rear central wall connecting the jaws together centrally, and distally from the front end surfaces, such that the rear wall and jaws define a longitudinal channel along the body's length, and the body has a generally U shaped cross section or profile along its longitudinal axis.

5. A device as claimed in claim 1, wherein each front end surface's width is such that it is capable of engaging one of the eyelids from medial canthus to lateral canthus of the user.

6. A device as claimed in claim 1, wherein each front end surface's width is equal to or less than 60 mm, 50 mm, 40 mm, 30 mm, 20 mm or 10mm.

7. A device as claimed in claim 1, wherein each front end surface is of a thickness that it is capable of engaging only tarsal plates of one of the eyelids, or is capable of engaging one whole eyelid.

8. A device as claimed in claim 7, wherein each front end surface has a thickness between 0.5 and 30 mm; 3 and 12 mm; 5 and 10 mm; or about 7, 8, or 9 mm.

9. A device as claimed in claim 1, wherein each front end surface has a variable thickness across its length, and wherein each front end surface is narrowed towards its termini so as to permit greater accuracy of manipulation of one of the eyelids near the one eyelid's canthi.

10. A device as claimed in claim 1, wherein each front end surface is bevelled or angled to increase contact with the eyelids.

11. A device as claimed in claim 1, wherein maximum height defined by the two jaws' outer extremities at each front end surface of the jaws which engages the eyelids is less than or equal to 40 mm, 35 mm, 30 mm, 25 mm, 20mm or 15 mm when the body of the device is in its relaxed form and where the front end surfaces are biased into a spaced relationship.

12. A device as claimed in claim 1, wherein the body's front in longitudinal view substantially defines:
    (i) a square or rectangle;
    (ii) rounded-corner square or rectangle;
    (iii) an arch having parallel lines on the jaws' top and bottom surfaces and curvature at one side and either an open or straight profile at the other side;
    (iv) a stadium having parallel lines on the jaws' top and bottom surfaces and curvature on the left and right sides; or
    (v) an elipse.

13. A device as claimed in claim 1 wherein the indentation, concave profile or groove has a nominal radius of between 10 to 20 mm.

14. A device as claimed in claim 1 wherein the upper and/or lower outer surfaces of the body incorporate one or two upstanding ridges.

15. A device as claimed in claim 1 wherein the upper and/or lower outer surfaces of the body incorporate a pad formed or affixed thereto which is designed and dimensioned to direct where the user's digits should compress the upper and/or lower outer surfaces to operate the device.

16. A device as claimed in claim 1, wherein the device includes an integrated switchable heating or vibrating mechanism.

17. A device as claimed claim 16 wherein the integrated heating mechanism comprises:
    (i) an integrated circuit incorporating a thermal sensor and a timer;
    (ii) heating elements; and
    (iii) an electrical power source.

18. A device as claimed in claim 1, wherein the body is composed of a single biocompatible material.

19. A device as claimed in claim 18 which is composed of, or composed essentially of, a material selected from: synthetic polymers; thermoplastic elastomers; silicone elastomers; styrene block copolymers; thermoplastic copolyesters; thermoplastic polyamides;
    thermoplastic olefins or polyolefins; thermoplastic polyurethanes; thermoplastic rubbers; and
    thermoplastic vulcanizates.

20. A device as claimed in claim 19 which is composed of, or composed essentially of heat transfer elastomeric silicon rubber.

21. A device as claimed in claim 1 which is composed of, or composed essentially of a material having a shore hardness of 22A and below.

22. A process for producing the body of the device as claimed in claim 1 which process comprises casting the body in a single mould or parts of the body multiple moulds, wherein where the parts of the body are cast in multiple moulds, the parts are subsequently joined.

23. A method for massaging the upper and/or lower lids of the eye, the method comprising:
    (i) providing a device as claimed in claim 1
    (ii) engaging the front end surfaces with the upper and lower eyelids; and
    (iii) bringing the front end surfaces into a proximate relationship, thereby causing at least one eyelid to be compressed toward the other.

24. A method as claimed in claim 23 which causes vertical motion on the eyelids which causes one or more meibomian glands to be compressed in a direction from peripheral gland to gland orifice causing compression and expression therefrom.

25. A method as claimed in claim 23 wherein movement of the front end surfaces is vertical and unidirectional and there is no reverse action, and the device is disengaged from the eye after the front end surfaces are brought together.

26. A method as claimed in claim 23 which is a manual method, whereby the device is operated using any combination of the user's digits on one or two hands.

27. A method as claimed in claim 23 which is performed in conjunction with heat treatment.

28. A method as claimed in claim 27 wherein the device is heated before or during use to between 35° C. and 45° C.

29. A method for manipulating the upper and/or lower lids of the eye, the method comprising:
    (i) providing a device as claimed in claim 1;
    (ii) engaging the front end surfaces with the upper and lower eyelids; and
    (iii) moving the front end surfaces,
    thereby causing at least one eyelid to be manipulated.

30. A method as claimed in claim 23 for use in the prevention, treatment or alleviation of dry eye or Meibomian Gland Dysfunction or a symptom thereof.

31. A device for massaging both upper and lower eyelids, the device comprising:
    a body, composed of flexible resilient biocompatible material,
    two jaws, which have an opposing relationship,
    wherein the jaws define an orifice, aperture or slot within the body,
    and wherein each jaw has a front end surface,
    and wherein the two jaws are biased into a spaced relationship by the material of the body, and wherein the front end surface of each jaw is adapted to engage either the upper or lower eyelid, such that movement of each front end surface causes movement of at least one of the upper and lower eyelids with respect to the other eyelid, whereby, in use, manually engaging the end surfaces of the jaws with the upper and lower eyelids and manually compressing outer surfaces of the jaws together brings the front end surfaces of the jaws into a proximate relationship, and thereby causes at least one eyelid to be compressed toward the other in a linear directional movement which causes one or more meibomian glands to be compressed in a direction from peripheral gland to gland orifice for expression of sebum therefrom, wherein the device is adapted so that the front end surfaces are brought together using one hand or two hands of a user, wherein the body's upper and lower outer surfaces include digit engaging, pads, profiles, grooves or ridges to facilitate compression of the front end surfaces together, wherein the jaws are substantially linear and substantially parallel to one another, wherein the device comprises a supporting rear wall distally from the front end surfaces which connects the jaws and biases the jaws into the spaced relationship, wherein the rear wall incorporates an indentation or concave profile or groove to receive one or more digits of the user.

32. A device as claimed in claim 31, wherein each front end surface's width is equal to or less than 60 mm, 50 mm, 40 mm, 30 mm, 20 mm or 10 mm.

33. A device as claimed in claim 31, wherein each front end surface is bevelled or angled to increase contact with one of the eyelids.

34. A device as claimed in claim 31, wherein the body is composed of a single biocompatible material.

35. A device as claimed in claim 31 wherein the upper and/or lower and/or rear outer surfaces of the body incorporate upstanding lugs whereby compression of lugs moves the jaws away from each other.

\* \* \* \* \*